(12) United States Patent
Shimizu et al.

(10) Patent No.: US 9,776,944 B2
(45) Date of Patent: Oct. 3, 2017

(54) PROCESS FOR PRODUCING ACETIC ACID

(75) Inventors: Masahiko Shimizu, Masahiko (JP);
Ryuji Saito, Otake (JP); Hiroyuki Miura, Himeji (JP); Takashi Ueno, Himeji (JP)

(73) Assignee: DAICEL CORPORATION, Osaka-Shi (JP)

( * ) Notice: Subject to any disclaimer, the term of this patent is extended or adjusted under 35 U.S.C. 154(b) by 143 days.

(21) Appl. No.: 13/993,109

(22) PCT Filed: Dec. 1, 2011

(86) PCT No.: PCT/JP2011/077847
§ 371 (c)(1),
(2), (4) Date: Jun. 11, 2013

(87) PCT Pub. No.: WO2012/086386
PCT Pub. Date: Jun. 28, 2012

(65) Prior Publication Data
US 2013/0264186 A1    Oct. 10, 2013

(30) Foreign Application Priority Data
Dec. 24, 2010 (JP) ................................. 2010-288523

(51) Int. Cl.
C07C 51/44    (2006.01)
C07C 51/50    (2006.01)

(52) U.S. Cl.
CPC ............. *C07C 51/44* (2013.01); *C07C 51/50* (2013.01)

(58) Field of Classification Search
CPC ......... C07C 51/12; C07C 51/42; C07C 51/44; C07C 51/50; C07C 53/08
(Continued)

(56) References Cited

U.S. PATENT DOCUMENTS 3,772,156 A    11/1973    Johnson et al.
4,267,124 A    5/1981    Hardy et al.
(Continued)

FOREIGN PATENT DOCUMENTS

EP    0632007 A1    1/1995
JP    48-061414 A    8/1973
(Continued)

OTHER PUBLICATIONS

Extended European Search Report, dated Jul. 23, 2014, for European Application No. 11851479.3.
(Continued)

*Primary Examiner* — Prem C Singh
*Assistant Examiner* — Brandi M Doyle
(74) *Attorney, Agent, or Firm* — Birch, Stewart, Kolasch & Birch, LLP

(57) ABSTRACT

A process for producing acetic acid including an acetic acid collection step for feeding a first distillation column with a volatile component at least containing acetic acid, methyl acetate, methyl iodide, water, and hydrogen iodide. Separating a first lower boiling point component as an overhead, and collecting a first liquid stream containing acetic acid. An acetic acid purification step for feeding a second distillation column with the first liquid stream, and separating a second lower boiling point component as an overhead. Collecting a second liquid stream containing acetic acid. An alkali component is added or mixed for distilling a mixture to be treated containing the first liquid stream and the alkali component in the second distillation column. In the mixture, at least one component (A) having a boiling point lower than acetic acid. The at least one component (A) having a concentration of 0.1 to 15% by weight.

14 Claims, 1 Drawing Sheet

(58) Field of Classification Search
USPC ...... 203/6, 7, 29, 33, 36, 37, 71, 74, 78, 80, 203/81, 82, DIG. 21; 562/608
See application file for complete search history.

(56) References Cited

U.S. PATENT DOCUMENTS

| | | |
|---|---|---|
| 5,576,458 A | 11/1996 | Minami et al. |
| 5,653,853 A | 8/1997 | Kagotani et al. |
| 2008/0214866 A1 | 9/2008 | Miura et al. |
| 2009/0036710 A1 | 2/2009 | Miura et al. |

FOREIGN PATENT DOCUMENTS

| | | |
|---|---|---|
| JP | 64-160313 A | 12/1979 |
| JP | 6-340576 A | 12/1994 |
| JP | 7-309800 A | 11/1995 |
| JP | 2006-160645 A | 6/2006 |
| JP | 2009-501129 A | 1/2009 |
| WO | WO 2006/062216 A1 | 6/2006 |
| WO | WO 2007/007891 A2 | 1/2007 |

OTHER PUBLICATIONS

International Search Report issued in PCT/JP2011/077847, dated Apr. 17, 2012.
International Preliminary Report on Patentability and the English translation of the Written Opinion of the International Searching Authority, dated Jul. 11, 2013, for Application No. PCT/JP2011/077847.
Japanese Office Action for Japanese Application No. 2012-549707, dated Oct. 27, 2015, with an English translation.

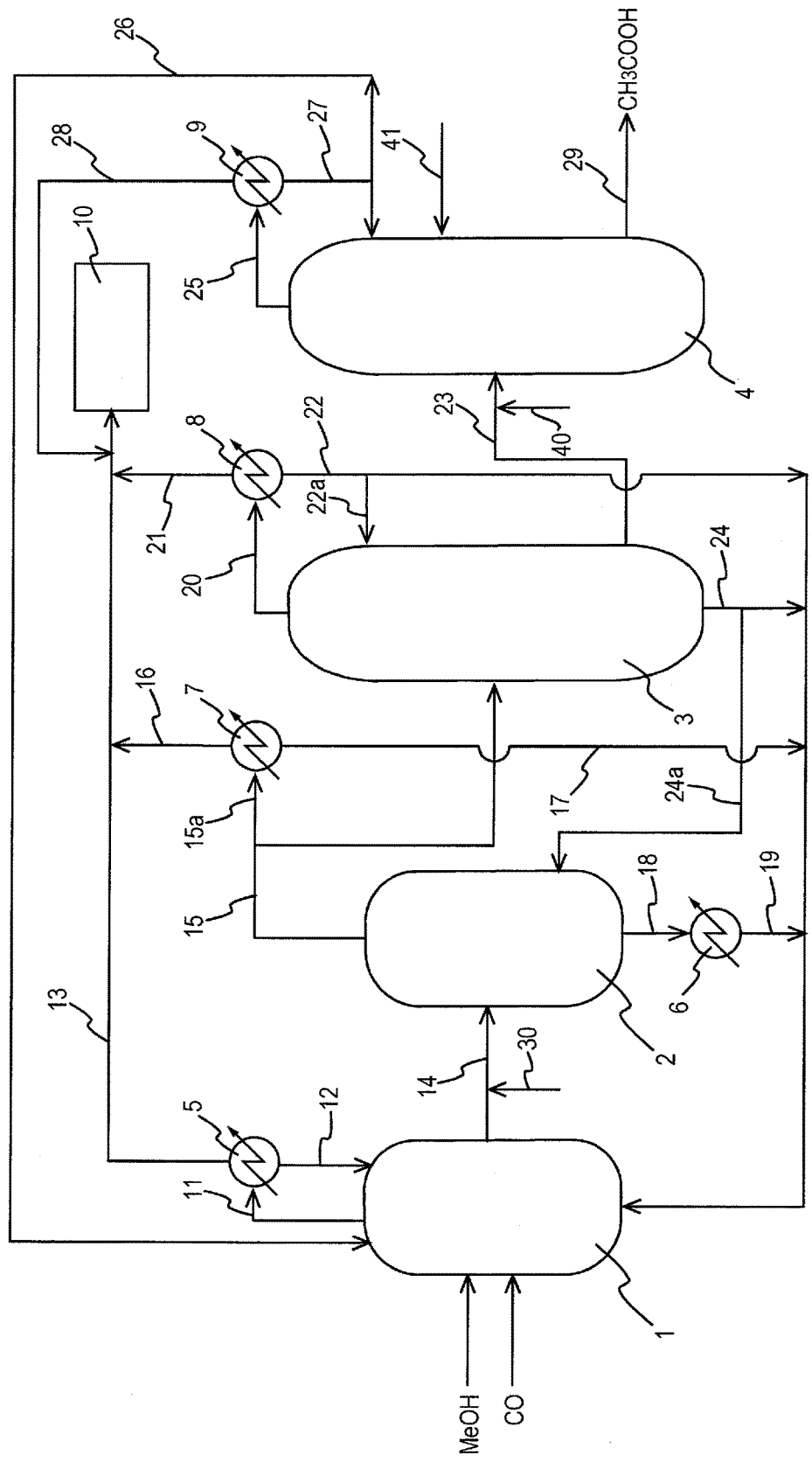

PROCESS FOR PRODUCING ACETIC ACID

TECHNICAL FIELD

The present invention relates to a process for producing acetic acid while efficiently inhibiting an increase in concentration of hydrogen iodide (or condensation of hydrogen iodide) in a distillation column (second distillation column) for purifying crude acetic acid by further distillation.

BACKGROUND ART

Various industrial production processes of acetic acid have been known. Among others, an industrially excellent process includes a process which comprises continuously allowing methanol to react with carbon monoxide with the use of a metal catalyst (such as a rhodium catalyst), an ionic iodide (e.g., lithium iodide), and methyl iodide in the presence of water to give acetic acid. Moreover, recently improvement in reaction conditions and catalysts was investigated, and an industrial process for producing acetic acid with a highly efficient production has been developed by addition of a catalyst stabilizer (such as an iodide salt) and the reaction under a low water content condition compared with the conventional condition.

Examples of the production process of acetic acid includes a process for producing purified acetic acid, which comprises allowing methanol to react with carbon monoxide, subjecting the resulting reaction mixture containing acetic acid to distillation (flash distillation) in a flash evaporator, subjecting a component vaporized by the distillation to a first distillation column to separate a liquid stream containing acetic acid as a main component and water, and others, subjecting the stream containing acetic acid to a second distillation column to remove water and others and separate an acetic acid stream as a liquid stream. In this process, condensation of hydrogen iodide in the first distillation column or the second distillation column may precipitate the corrosion of the distillation column. Since it is preferable the increase in concentration of hydrogen iodide in the distillation column be inhibited, the decrease in concentration of hydrogen iodide in the distillation column is being attempted.

For example, Japanese Patent Application Laid-Open No. 2006-160645 (JP-2006-160645A, Patent Document 1) discloses a process for distilling a mixture containing hydrogen iodide and water, which comprises distilling the mixture having a water content of not more than 5% by weight in a distillation system to prevent condensation of hydrogen iodide in the distillation system. With respect to a mixture applying the process, the document discloses that the process can be applied to alight component which is separated from the reaction mixture by a first distillation (distillation by a flash evaporator or the like) and is rich in a low boiling point component (e.g., water, an alcohol, an alkyl iodide, a carboxylic acid or an acid anhydride thereof, a carboxylate ester, and hydrogen iodide). In the process described in the document, however, the concentration of hydrogen iodide is reduced by adjusting the concentration of water based on the equilibrium theory, and there are limitations to the decrease in the concentration of hydrogen iodide. Thus it is difficult to decrease the concentration of hydrogen iodide at a high level. Moreover, since the process described in the document is applied to a light component obtained through a flash distillation, the condensation of hydrogen iodide in a distillation column for further purifying acetic acid separated from the light component cannot be inhibited.

Moreover, Japanese Patent Application Laid-Open No. 2009-501129 (JP-2009-501129A, Patent Document 2) discloses a process for producing purified acetic acid, which comprises feeding an acetic acid stream containing acetic acid, a hydrogen halide, a lower boiling point component and a higher boiling point component to a first distillation column, separating a lower boiling point stream containing part of the lower boiling point component and a higher boiling point stream containing part of the higher boiling point component in the first distillation column, withdrawing a side stream containing at least acetic acid by side cut, feeding the side stream to a second distillation column, separating a lower boiling point stream containing part of the lower boiling point component and a higher boiling point stream containing part of the higher boiling point component in the second distillation column, and withdrawing a side stream containing acetic acid by side cut to collect (or recover) acetic acid; which further comprises feeding (i) the first distillation column with water, or water and at least one first component (A) selected from the group consisting of an alcohol corresponding to the carboxylic acid and having "n" carbon atom(s), and an ester of the alcohol with the carboxylic acid or (ii) the first distillation column with the first component (A) with from a height level (position) lower than a side stream port for conducting side cut of the side stream containing the carboxylic acid having "n+1" carbon atoms.

This document discloses that at least one second component (B) selected from the group consisting of (b-1) methanol, (b-2) methyl acetate, (b-3) an alkali metal hydroxide (e.g., potassium hydroxide), (b-4) an alkali metal acetate (e.g., potassium acetate), and (b-5) a hypophosphorous acid can usually be fed to the second distillation column from at least one position upper or lower than a side cut port (side stream port) for conducting side cut of the acetic acid stream in order to reduce the concentration of hydrogen iodide contained in the acetic acid stream withdrawn by side cut and prevent the condensation of hydrogen iodide in the distillation column. In Examples of the document, potassium hydroxide is fed to the second distillation column at a height level (or plate) lower than the side stream port or at a height level (or plate) which is upper than the side stream port and lower than a feed port for feeding the acetic acid stream to the second distillation column.

The process described in the document achieves the condensation of hydrogen iodide in the second distillation column to some extent. However, hydrogen iodide is contained in the acetic acid stream to be fed to the second distillation column and is moved together with water to an upper part (or top) of the second distillation column by distillation, while potassium hydroxide or the like is moved downward. Therefore, when potassium hydroxide is fed to the second distillation column at a height level lower than a port for feeding the acetic acid stream to the second distillation column as described in the document, it is difficult to efficiently inhibit the condensation of hydrogen iodide in the upper part (or top) of the second distillation column. Moreover, in the process described in the document, although the second component (B) is fed in order to decrease hydrogen iodide contained in the side cut stream fed from the first distillation column, in an actual system not only hydrogen iodide contained in the side cut stream but also hydrogen iodide newly produced by a reaction of methyl iodide with water, and other reactions in the upper part of the second distillation column exists in the second distillation column. The condensation of hydrogen iodide existing in the upper part of the distillation column cannot be inhibited using potassium hydroxide or the like efficiently. According to the process described in the document, even if the quality of acetic acid can be improved by reducing the concentration of hydrogen iodide (HI) contained in the side cut stream, it is difficult to reduce the concentration of hydrogen iodide at a high level in the whole second distillation column. Further, the concentration of hydrogen iodide in the whole second distillation column may be reduced by feeding an alkali metal hydroxide (e.g., potassium hydroxide) at a height level lower than the feed port of the second distillation column and feeding an alcohol (e.g., methanol) at the same time (or the same position) the alkali metal hydroxide or at a position lower than the feeding position of the alkali metal hydroxide. In this case, however, a distillation column having a large column diameter is necessary, and the process is inefficient.

Incidentally, Japanese Patent Application Laid-Open No. 48-61414 (JP-48-61414A, Patent Document 3) discloses a method for removing (or separating) iodine from acetic acid, which comprises introducing an acetic acid stream containing iodine as an impurity into a middle part of both ends of a first distillation column, introducing an alkali metal or alkaline earth metal compound (an oxide, a hydroxide, a carbonate, a bicarbonate, or a weak organic acid salt of an alkali metal or alkaline earth metal) into the middle part of both ends of the first distillation column, withdrawing an overhead product stream from the first distillation column, introducing the product stream into a middle part of both ends of a second distillation column, and withdrawing an acetic acid stream substantially free from iodine from a lower part of the second distillation column and withdrawing an overhead fraction containing iodine from the second distillation column.

According to the method described in the document, the alkali metal or alkaline earth metal compound is fed to the product stream from the first distillation column or the second distillation column. However, the product streams are overheads in the first and second distillation columns, and this method is quite different in production process of acetic acid from the above-mentioned process for separating the acetic acid stream as a liquid component. For example, the method described in the document intends to decrease hydrogen iodide contained in a purified product stream, and the method is quite different in liquid to be treated from the above-mentioned process.

RELATED ART DOCUMENTS

Patent Documents

Patent Document 1: JP-2006-160645A (Claims, Paragraph No. [0027], and Examples)
Patent Document 2: JP-2009-501129A (Claims, Paragraph Nos. [0047] and [0142] to [0147])
Patent Document 3: JP-48-61414A (Claims and Drawings)

SUMMARY OF THE INVENTION

Problems to be Solved by the Invention

It is therefore an object of the present invention to provide a process for producing acetic acid while efficiently inhibiting (or preventing) an increase in concentration of hydrogen iodide (or condensation of hydrogen iodide) in a distillation column (second distillation column) for purifying crude acetic acid, from which a lower boiling point has been removed by distillation, by further distillation.

It is another object of the present invention to provide a process for producing acetic acid, the process preventing corrosion of a second distillation column.

Means to Solve the Problems

The inventors of the present invention made intensive studies to achieve the above objects and finally found that, in a process for producing acetic acid which comprises separating a lower boiling component from a volatile component at least containing acetic acid, methyl acetate, methyl iodide, and hydrogen iodide by distillation, feeding a second distillation column (dehydration column) with the resulting crude acetic acid, and separating water and others to obtain purified acetic acid, the condensation of hydrogen iodide in the whole second distillation column can be inhibited (or prevented) at a high level by adding an alkali component to crude acetic acid in a specific embodiment and subjecting the mixture to distillation; and that the inhibition of the condensation can inhibit the corrosion of the whole second distillation column. The present invention was accomplished based on the above findings.

That is, the process of the present invention includes a process for producing acetic acid, which comprises an acetic acid collection step for feeding a first distillation column with a volatile component at least containing acetic acid, methyl acetate, methyl iodide, water, and hydrogen iodide, separating a first lower boiling point component as an overhead (volatile component or vaporized component), and collecting a first liquid stream (crude liquid acetic acid stream, first liquid component) mainly containing acetic acid, and an acetic acid purification step for feeding a second distillation column with the first liquid stream, further separating a second lower boiling point component as an overhead, and collecting a second liquid stream (purified liquid acetic acid stream, second liquid component) containing acetic acid; wherein an alkali component is added or mixed in the following manners (1) and/or (2) for distilling a liquid object to be treated (or a liquid object) containing the first liquid stream and the alkali component in the second distillation column (or the first liquid stream is subjected to distillation in the presence of the alkali component):

(1) the alkali component is added to or mixed with the first liquid stream before the first liquid stream is fed to the second distillation column, (2) in the second distillation column, the alkali component is added or mixed at the same height level (or position) as a height level (or position) at which the first liquid stream is fed or at a height level (or position) upper than the height level (or position) at which the first liquid stream is fed.

Incidentally, in the manner (2), the feeding position of the first liquid component is usually situated at a position upper than a position at which the second liquid component is collected (withdrawn as a bottom fraction or as side cut fraction) from the second distillation column.

For the manner, probably because hydrogen iodide in the first liquid component is easily allowed to contact or react with the alkali component (neutralization) in the second distillation column before the alkali component is moved to the lower part of the second distillation column, the condensation of hydrogen iodide in the whole second distillation column can efficiently be inhibited.

According to the process of the present invention, the first lower boiling point component is separated by the first distillation column. For example, in the first liquid component, the concentration of methyl iodide may be about 10 ppm to 8% by weight [for example, less than 4% by weight (e.g., about 10 ppm to 3.5% by weight)], the concentration of methyl acetate may be about 0.1 to 8% by weight, the concentration of water may be about 0.2 to 20% by weight (particularly, not more than 3% by weight), and the concentration of hydrogen iodide may be not more than 1000 ppm on the basis of weight (e.g., not more than 100 ppm, preferably about 1 to 30 ppm). Moreover, the amount to be added of the alkali component may for example be about 1 to 2000 molar equivalents relative to 1 mol of hydrogen iodide in the first liquid stream, and the alkali component may be added in order that the concentration of the alkali component in the liquid object may be not more than 100000 ppm on the basis of weight.

In the manner (1), the contact temperature of the first liquid stream (or component) and the alkali component may be about 100 to 170° C., and the time from when the first liquid stream (or component) and the alkali component are mixed till when the mixture is fed to the second distillation column may be not more than 5 minutes.

According to the present invention, since the alkali component is added in a specific manner, the alkali component can be used for neutralization of hydrogen iodide certainly, so that the amount to be added of the alkali component can be reduced. Therefore, the condensation or accumulation of an excessive amount of the alkali component in the second distillation column (e.g., a lower part of the distillation column) can efficiently be inhibited. For example, in the process, the amount to be added of the alkali component may be not more than 85 molar equivalents (e.g., not more than 80 molar equivalents) relative to 1 mol of hydrogen iodide in the first liquid stream, and the alkali component may be added in order that the concentration of the alkali component in the liquid object may be not more than 1000 ppm (e.g., not more than 800 ppm) on the basis of weight.

According to the present invention, a second distillation may be performed in the presence of the added alkali component and at least one component (A) having a boiling point lower than the boiling point of acetic acid and being selected from the group consisting of an alcohol, an ether, and an acetate ester. Since the component (A) tends to exist in an upper part of the distillation column, the tendency and the neutralization with the alkali component are combined to efficiently inhibit the production of hydrogen iodide due to a reaction of methyl iodide with water in the upper part of the second distillation column. In the manner, for example, the liquid object in which the component (A) at a concentration of not less than 0.2% by weight (e.g., not less than 1% by weight) exists may be distilled in the second distillation column.

Representatively, the component (A) may be a component containing at least one member selected from the group consisting of methanol, dimethyl ether, and methyl acetate.

The component (A) may be contained in the first liquid stream (for example, when methyl acetate is contained at a sufficient concentration in the first liquid stream), or may newly (or separately) be added. That is, the component (A) may be allowed to exist in the liquid object by adding the component (A) to the first liquid stream. Representatively, the component (A) may be allowed to exist in the liquid object by (i) adding the component (A) to the first liquid stream before the first liquid stream is fed to the second distillation column and/or (ii), in the second distillation column, adding the component (A) to the first liquid stream at the same height level (or position) as a height level (or position) at which the first liquid stream is fed (for example, a plate to be fed or supplied) or at a height level (or position) upper than the height level at which the first liquid stream is fed [for example, a plate upper than (e.g., the first plate above) a plate at which the first liquid stream is fed].

In the process of the present invention, the material of (or for forming) the second distillation column may comprise an alloy (for example, a nickel-based alloy). The present invention achieves the inhibition of the corrosion, and even a second distillation column made of such a relatively corrosive material can preferably be used.

The process of the present invention usually further comprises a reaction step for continuously allowing methanol to react with carbon monoxide in the presence of a catalyst system comprising a metal catalyst, an ionic iodide (e.g., an alkali metal iodide such as lithium iodide), and methyl iodide in a carbonylation reactor, and a flash distillation step for continuously feeding a flasher (flash evaporator) with a reaction mixture from the reactor and evaporating a volatile component at least containing product acetic acid, methyl acetate, methyl iodide, water, and hydrogen iodide by flash distillation, and the volatile component obtained through these steps is fed to the first distillation column.

For the process comprising the flash distillation step, in the flash distillation step, the reaction mixture may be separated into the volatile component and a liquid catalyst mixture at least containing the metal catalyst and the ionic iodide, the flash distillation may be conducted under the condition that the concentration of methyl acetate is not less than 0.6% by weight. Probably because the flash distillation under the condition can inhibit an increase in concentration of hydrogen iodide in the flash evaporator and additionally can efficiently increase in concentration of methyl acetate in the second distillation column, the increase in concentration of hydrogen iodide in the second distillation column can further efficiently be inhibited.

The concentration of methyl acetate in the liquid catalyst mixture may be not less than 1% by weight (in particular, not less than 1.5% by weight). Moreover, the concentration of water in the liquid catalyst mixture may be not more than 15% by weight. The concentration of the metal catalyst in the liquid catalyst mixture may be not less than 300 ppm on the basis of weight. Further, the concentration of acetic acid in the liquid catalyst mixture may be not less than 40% by weight.

Representatively, with respect to the concentration of each component in the liquid catalyst mixture, the concentration of the ionic iodide may be not more than 50% by weight, the concentration of methyl iodide may be not more than 5% by weight, the concentration of acetic acid may be about 45 to 90% by weight, and the concentration of water may be not more than 10% by weight. In particular, with respect to the concentration of each component in the liquid catalyst mixture, the concentration of the ionic iodide may be not more than 40% by weight, the concentration of methyl iodide may be about 0.01 to 4% by weight, the concentration of acetic acid may be about 50 to 85% by weight, the concentration of methyl acetate may be about 0.7 to 5% by weight, and the concentration of water may be about 0.8 to 8% by weight.

In the flash distillation step, the flash distillation may be conducted at an absolute pressure of about 0.1 to 0.5 MPa, and the temperature of the liquid catalyst mixture (or the flash distillation temperature) may be about 100 to 170° C.

In the process of the present invention, the concentration of each component in the flash evaporator may be adjusted by adding each component or component(s) for producing each component. For example, the concentration of methyl acetate in the liquid catalyst mixture may be adjusted (for example, adjusted to not less than 0.6% by weight) by adding or mixing methyl acetate and/or a component producing methyl acetate to the reaction mixture and/or the flash evaporator.

Throughout the description, the total of the proportion(s) of any component(s) existing in the same mixture system (such as the first liquid fraction) is not more than 100% by weight; and the proportions of the all components is 100% by weight in total.

Effects of the Invention

According to the process of the present invention, acetic acid can be produced while efficiently inhibiting (or preventing) an increase in concentration of hydrogen iodide in a distillation column (second distillation column) for purifying crude acetic acid, from which a lower boiling point has been removed by distillation, by further distillation. Moreover, according to the present invention, the corrosion of the second distillation column can be inhibited. Therefore, distillation can efficiently be performed without forming the second distillation column with a high-quality material having a high corrosion-resistance. Thus according to the present invention, the second distillation column can be made of an inexpensive or low-grade material, so that the cost of the production process of acetic acid can efficiently be reduced.

BRIEF DESCRIPTION OF DRAWINGS

FIG. 1 is a diagram for explaining a production process (or production apparatus) of acetic acid in accordance with an embodiment of the present invention.

DESCRIPTION OF EMBODIMENTS

Hereinafter, the present invention will be explained in detail with reference to the drawings. FIG. 1 is a diagram (a flow sheet, a schematic process drawing, or a schematic plant layout drawing) for explaining a production process (or production apparatus) of acetic acid in accordance with an embodiment of the present invention.

The embodiment of FIG. 1 shows a continuous process (or apparatus) for producing acetic acid from a liquid reaction medium (or reaction mixture) generated by a continuous carbonylation reaction of methanol with carbon monoxide in the presence of a catalyst system comprising a rhodium catalyst as a metal catalyst and a co-catalyst [lithium iodide as an ionic iodide (or iodide salt) and methyl iodide], as well as acetic acid, methyl acetate, and a finite amount of water.

The process (or production apparatus) comprises a reactor (reaction system) 1 for carrying out the above-mentioned carbonylation reaction of methanol; a flasher or evaporator (flash evaporator) 2 for separating a volatile component or an acetic acid stream (a lower boiling point fraction) at least containing product acetic acid, methyl acetate, methyl iodide, water, and by-product hydrogen iodide, and a liquid catalyst mixture (a low-volatile component or a higher boiling point fraction) mainly containing a catalyst component (a higher boiling point component) (e.g., a rhodium catalyst and lithium iodide) from a liquid reaction medium (or a reaction mixture or a reaction solution) which is introduced from the reactor 1 through a feed line 14 and contains acetic acid generated by the reaction; a first distillation column (splitter column) 3 for separating or removing at least part of a lower boiling point fraction (first lower boiling point fraction) containing a lower boiling point component (e.g., methyl iodide, methyl acetate, and acetaldehyde) out of the volatile component introduced from the flasher 2 through a feed line 15 as an overhead from a column top thereof and withdrawing or discharging a first liquid stream containing acetic acid (an acetic acid stream, crude acetic acid stream) as a side stream by side cut; a second distillation column 4 for removing at least part of a lower boiling point fraction (second lower boiling point fraction) containing a lower boiling point component (such as water) as an overhead from a column top thereof out of the acetic acid stream introduced from the first distillation column 3 through a feed line 23 by side cut, separating at least part of a higher boiling point component (higher boiling point impurities) (containing, e.g., water and propionic acid) from a bottom of the column, and obtaining a second liquid stream containing acetic acid (an acetic acid stream, purified acetic acid stream) through a feed line 29 as a side stream by side cut.

This process is provided with a condenser or a heat exchanger for condensing a component fed through each line. Specifically, the reactor 1 is equipped with a condenser 5 for condensing a condensable component in an offgas (vapor) discharged through a discharge line 11; a recycle line 12 for recycling a liquid component condensed by the condenser 5 to the reactor 1; and a discharge line 13 for discharging a gaseous component, which is a non-condensed component in the condenser 5.

Further, the flasher 2 is equipped with a heat exchanger 6 for cooling a liquid catalyst mixture (or bottom fraction) separated by the flasher 2 and discharged from the bottom of the flasher 2 through a discharge line 18; a recycle line 19 for recycling the liquid catalyst mixture cooled by the heat exchanger 6 to the reactor 1; a heat exchanger 7 for condensing a condensable component in part of the volatile component (or volatile phase) discharged as an overhead from the flasher 2 and introduced through a feed line 15a; a discharge line 16 for discharging a gaseous component, which is a non-condensable component in the heat exchanger 7; and a recycle line 17 for recycling a liquid (or liquefied) component containing acetic acid condensed by the heat exchanger 7 to the reactor 1.

Furthermore, the first distillation column 3 is equipped with a condenser 8 for condensing a condensable component in the lower boiling point fraction or overhead discharged through a discharge line 20; a recycle line 22 for recycling a liquid component condensed by the condenser 8 to the reactor 1; a recycle line 22a for recycling (or refluxing) part of the liquid component condensed by the condenser 8 to the first distillation column 3; a discharge line 21 for discharging a gaseous component, which is a non-condensable component in the condenser 8; and a line 24 for discharging a higher boiling point fraction in the first distillation column 3 and recycling the higher boiling point fraction to the reactor 1. Incidentally, the liquid component recycled to the first distillation column 3 is used for refluxing in the first distillation column 3.

The second distillation column 4 is equipped with a condenser 9 for condensing a condensable component in the lower boiling point fraction or overhead discharged through a discharge line 25; a recycle line 27 for recycling (or refluxing) a liquid component or lower boiling point fraction condensed by the condenser 9 to the second distillation column 4; a discharge line (recycle line) 26 for separating part or all of the liquid component or lower boiling point fraction condensed by the condenser 9 from the line 27 and recycling the separated component or fraction to the reactor 1; and a line 28 for feeding a gas separated in the condenser 9 to a scrubber 10 through a line 13.

This process shown in FIG. 1 further comprises a scrubber or scrubber system 10 for recovering the gaseous components (or non-condensed components) or others discharged from the condenser 5, the heat exchanger 7, and the condenser 8 and abandoning the components and/or recycling the components to the reaction system (e.g., the reactor 1). Incidentally, a line for recycling the gaseous component or others from the scrubber system 10 to the reaction system (e.g., the reactor 1) is omitted in FIG. 1.

Hereinafter, the process shown in FIG. 1 will be explained in more detail.

Methanol as a liquid component and carbon monoxide as a gaseous reactant may be continuously fed to the reactor 1 at a predetermined rate, and a catalyst mixture (a liquid catalyst mixture) containing a carbonylation catalyst system [a catalyst system comprising a main catalyst component (e.g., a rhodium catalyst) and a co-catalyst (e.g., lithium iodide and methyl iodide)] and water may be continuously fed to the reactor 1. Moreover, fraction(s) (e.g., in the form of liquid) containing lower boiling point fraction(s) and/or higher boiling point fraction (s) from the succeeding step (s) (e.g., the flasher 2, the first and second distillation columns 3 and 4, the heat exchanger 7, and the scrubber system 10) may also be fed to the reactor 1. Then, inside the reactor 1, a liquid-phase reaction system containing the reactant and the higher boiling point component such as the metal catalyst component (e.g., a rhodium catalyst) and the ionic iodide (e.g., lithium iodide) is in equilibrium with a vapor-phase system comprising carbon monoxide, by-products by the reaction (hydrogen, methane, carbon dioxide), and a vaporized lower boiling point component (e.g., methyl iodide, acetic acid as a product, and methyl acetate), and a carbonylation reaction of methanol proceeds under stirring by a stirrer or other means.

The inner pressure of the reactor 1 (e.g., reaction pressure, carbon monoxide partial pressure, hydrogen partial pressure, methane partial pressure, and nitrogen partial pressure) may be maintained at a constant pressure by withdrawing a vapor from the column top and introducing the withdrawn vapor into the condenser 5. The withdrawn vapor is cooled by the condenser 5 to give a liquid component (containing acetic acid, methyl acetate, methyl iodide, acetaldehyde, water, and others) and a gaseous component (containing carbon monoxide, hydrogen, and others). The resulting liquid component is recycled to the reactor 1, and the resulting gaseous component (waste gas) is discharged to the scrubber system 10, and if necessary, recycled to the reactor 1. In particular, the reaction system is an exothermic reaction system that accompanies heat generation, and part of the quantity of heat generated in the reactor may be removed by cooling part of the reaction heat transferred from the reaction solution to the vapor with the condenser 5.

To the reactor 1, if necessary, hydrogen may be fed in order to increase the catalytic activity. Moreover, since the reaction system is an exothermic reaction system that accompanies heat generation, the reactor 1 may be equipped with a heat-removable (or heat-removing) or cooling unit (e.g., a jacket) for controlling a reaction temperature. Incidentally, as described later, the process of FIG. 1 is equipped with a heat exchanger 7 for removing heat from part of a volatile component from the flash evaporator 2. Thus even when the reactor is not equipped with the heat-removable or cooling unit, the heat can be removed.

Components contained in the reaction mixture (crude reaction solution) generated in the reactor 1 may include acetic acid, hydrogen iodide, a lower boiling point component or lower boiling point impurity having a boiling point lower than that of acetic acid (e.g., methyl iodide as a co-catalyst, methyl acetate as a reaction product of acetic acid with methanol, and acetaldehyde, crotonaldehyde, 2-ethylcrotonaldehyde, and a higher iodide (such as hexyl iodide or decyl iodide) as by-products), and a higher boiling point component or higher boiling point impurity having a boiling point higher than that of acetic acid [a metal catalyst component (a rhodium catalyst, and lithium iodide as a co-catalyst), propionic acid, and water].

In order to mainly separate the higher boiling point component (such as the metal catalyst component) from the reaction mixture, the reaction mixture (or part of the reaction mixture) is continuously withdrawn from the reactor 1 and introduced or fed into the flasher (evaporator) 2. In the flasher 2, a volatile component or a lower boiling point fraction (mainly containing acetic acid which is a product and also functions as a reaction solvent, methyl acetate, methyl iodide, water, hydrogen iodide, and others) is evaporated by flash distillation to separate a liquid catalyst mixture or a higher boiling point fraction (mainly containing a metal catalyst component, e.g., a rhodium catalyst, lithium iodide, and others) from the reaction mixture. Incidentally, in the liquid catalyst mixture, the metal catalyst component, and in addition, components remaining without evaporation (e.g., acetic acid, methyl iodide, water, and methyl acetate) are also contained.

Inside of the flasher 2, the flash distillation may be carried out so that at least methyl acetate in the liquid catalyst mixture may be maintained at a predetermined concentration (e.g., not less than 0.1% by weight, particularly, not less than 0.6% by weight). The flash distillation under the condition prevents the concentration of hydrogen iodide in the flash evaporator from rising. Thus the corrosion of the flash evaporator is markedly prevented. In addition, the adjustment of the methyl acetate concentration allows the concentration of hydrogen iodide to be reduced efficiently while increasing the concentration of methyl acetate in the first liquid stream. As a result, a more efficient reduction of the concentration of hydrogen iodide in the second distillation column is achieved. Incidentally, the concentration of methyl acetate may for example be adjusted by increasing the concentration of methanol in the reaction mixture and allowing the reaction of methanol with acetic acid to proceed predominantly, and others. If necessary, the concentration of methyl acetate may be adjusted by feeding methyl acetate and/or a component for producing methyl acetate (for example, methanol and dimethyl ether) to the flash evaporator 2. In the embodiment of the FIGURE, a line 30, which joins the line 14, is provided. If necessary, the concentration of methyl acetate in the flash evaporator can also be adjusted by mixing methyl acetate and/or a component producing methyl acetate through the line 30 with the reaction mixture from the reactor 1.

The liquid catalyst mixture is continuously discharged from the bottom of the column. The discharged liquid catalyst mixture may directly be recycled to the reactor 1. In the embodiment shown in the FIGURE, the discharged liquid catalyst mixture is heat-removed (cooled) in the heat exchanger 6 and then recycled to the reactor 1.

On the other hand, the volatile component or lower boiling point fraction (acetic acid stream) is withdrawn from the column top or upper part of the flasher 2 and fed or introduced into the first distillation column 3, and part of the volatile component is introduced into the heat exchanger 7 to be condensed. The volatile component cooled by the heat exchanger 7 produces a liquid component (containing acetic acid, methanol, methyl iodide, methyl acetate, water, propionic acid, acetaldehyde, and others) and a gaseous component (containing carbon monoxide, hydrogen, and others). The resulting liquid component is recycled to the reactor 1. The resulting gaseous component (waste gas) is fed to the scrubber system 10, and if necessary, carbon monoxide is obtained without purification of the gaseous component or with purification thereof by PSA (pressure swing adsorption) method, and recycled to the reactor 1. The lower boiling point fraction is withdrawn from the flasher to introduce into the heat exchanger, and part of the reaction heat transferred from the reaction solution to the flash vapor is cooled by the heat exchanger. Accordingly, the heat can efficiently be removed. Thus, since the succeeding distillation column or condenser can be downsized (or miniaturized) even for a large-sized plant, acetic acid can be produced with a high purity and a high yield in a resource-saving and energy-saving equipment. Further, the heat can be removed without installing an external circulation cooling unit in the reactor, which leads to the prevention of carbon monoxide loss and the improvement of the reaction efficiency or the cost reduction of equipment.

Incidentally, by making (keeping) the inner temperature and/or pressure of the flasher 2 lower than those of the reactor 1, further generation of by-products or deterioration of the catalytic activity may be inhibited.

In the first distillation column 3, usually, the lower boiling point component (or fraction) containing the lower boiling point component (containing methyl iodide, methyl acetate, acetaldehyde, water, and others) is separated as an overhead from the top or upper part of the column and fed to the condenser 8, and a higher boiling point fraction (a first higher boiling point component) containing the higher boiling point component (e.g., propionic acid, an entrained catalyst, and lithium iodide) is separated from the bottom or lower part of the column through a bottom line 24 and recycled to the reactor 1.

The first lower boiling point component (lower boiling point fraction or overhead) withdrawn from the top or upper part of the first distillation column 3 contains acetic acid and others, and is fed to the condenser 8. The lower boiling point fraction withdrawn from the first distillation column 3 can be condensed by the condenser 8 to cool part of the reaction heat transferred from the reaction solution to the lower boiling point fraction through the flash vapor with the condenser 8, and thus part of the reaction heat can be removed. In the condenser 8, the lower boiling point fraction is condensed to separate a gaseous component mainly containing carbon monoxide, hydrogen and others, and a liquid component containing methyl iodide, methyl acetate, acetic acid, acetaldehyde and others. The gaseous component separated in the condenser 8 is fed to the scrubber system 10, and if necessary, carbon monoxide is obtained without purification of the gaseous component or with purification thereof by PSA (pressure swing adsorption) method and the gaseous component is recycled to the reaction system (e.g., the reactor 1) (not shown). The liquid component separated in the condenser 8 may be recycled to the first distillation column 3 through the line 22a. Incidentally, the liquid component may be a uniform solution or a separated solution (for example, a two-phase solution) system. For example, for the liquid component containing a predetermined amount of water, the liquid component may be separated into two phases composed of an aqueous phase (aqueous layer or water phase) and an oily phase (organic layer or organic phase), where the aqueous phase contains acetic acid, acetaldehyde, and others, and the oily phase contains methyl iodide and others. Moreover, the oily phase may be recycled to the reactor 1 and/or the first distillation column 3, and the aqueous phase (water phase) may be recycled to the reactor 1 and/or the first distillation column 3.

Moreover, the first higher boiling point fraction (or component) contains the higher boiling point component, as well as the lower boiling point component which remains without evaporation, acetic acid, and others. Part of the higher boiling point fraction discharged through the line 24 may be recycled to the flasher 2 through a line 24a, if necessary.

Further, the first liquid stream (side stream, acetic acid stream) mainly containing acetic acid is withdrawn from the first distillation column 3 and is fed or introduced into the second distillation column 4. From the acetic acid stream (first liquid stream) which is obtained by side cut from the first distillation column 3 and is fed to the second distillation column 4, a lower boiling point component (e.g., water) remaining in the acetic acid stream is further separated in the second distillation column 4, and an acetic acid stream having a higher purity (purified acetic acid stream) is withdrawn as a side stream.

The first liquid stream usually contains acetic acid, and in addition, components (e.g., methyl iodide, methyl acetate, water, and hydrogen iodide) which remains without separation in the first distillation column. When the first liquid stream containing these components is subjected to distillation, hydrogen iodide is condensed in the second distillation column. Hydrogen iodide is contained in the first liquid component and is also produced by a reaction of methyl iodide with water, and condensed in the second distillation column. In particular, hydrogen iodide is easily moved together with water to the upper part (or top) of the second distillation column and condensed. Moreover, the reaction of methyl iodide with water tends to occur in the upper part of the second distillation column.

Thus in the second distillation column, the first liquid stream is subjected to distillation in the presence of the alkali component (e.g., an alkali metal hydroxide such as potassium hydroxide). That is, the alkali component is added to or mixed with to the first liquid component through a line 40 and/or a line 41, and the liquid object containing the first liquid component and the alkali component is subjected to distillation in the second distillation column. Specifically, the alkali component is added to the first liquid component before the first liquid component is fed to the second distillation column through the line 40, which joins the line 23, and/or the alkali component is added to the first liquid component in the second distillation column 4 in the manner that the alkali component is fed at a height level (or a plate) upper or higher than the feed line 23. The addition of the alkali component in the manners allows neutralization of hydrogen iodide before hydrogen iodide is moved to the upper part of the second distillation column, even if an alkali component which is easily moved to the lower part of the distillation column is used. Therefore, the condensation of hydrogen iodide in the whole distillation column, including not only the lower part of the distillation column but also the upper part thereof, can efficiently be inhibited.

Moreover, in the second distillation column, the first liquid component may be subjected to distillation in the presence of the alkali component and at least one component (A) having a boiling point lower than the boiling point of acetic acid and being selected from the group consisting of an alcohol (e.g., methanol), an ether (e.g., dimethyl ether), and an acetate ester (e.g., methyl acetate). Incidentally, the component (A) may be contained in the first liquid component or may be added in the line 40 and/or the line 41. In order to allow the component (A) to exist at a sufficient concentration in the first liquid component, it is preferable that the component (A) be added in the line 40 and/or the line 41. As described above, the alkali component is easily moved to the lower part of the distillation column, and the reaction of methyl iodide with water tends to occur in the upper part of the distillation column. Accordingly, the alkali component existing in the upper part of the distillation column sometimes decreases depending on the adding position (or height level). The component (A) has a low boiling point, is easily moved to the upper part of the distillation column, and can consume hydrogen iodide (or can inhibit the production of hydrogen iodide) by the reaction, and the addition of the component (A) in combination with the alkali component allows the condensation of hydrogen iodide to be inhibited in the upper part of the distillation column further certainly.

In the second distillation column 4, a second lower boiling point component (lower boiling point fraction) containing the lower boiling point component is fed as an overhead from the top or upper part of the column to the condenser (holding tank) 9, and a second liquid stream (side stream, acetic acid stream) rich in acetic acid is distilled by side cut. If necessary, the lower boiling point fraction discharged from the top or upper part of the column may be recycled to the second distillation column 4 and/or the reaction system 1. Water may be separated as a lower boiling point component in the second distillation column 4, or may be mainly separated in the first distillation column 3 and further separated in the second distillation column 4 for purification. Incidentally, a higher boiling point fraction (a second higher boiling point component) such as a higher boiling point component (e.g., propionic acid) may be discharged from the bottom or lower part of the column, and if necessary, may be recycled to the reactor 1 or may be wasted out of the system (not shown). Moreover, second liquid stream may further be subjected to distillation for purification.

The lower boiling point fraction withdrawn from the top or upper part of the second distillation column 4 contains methyl iodide, methyl acetate, water, acetaldehyde, and others, and is condensed by the condenser 9. Then the lower boiling point fraction condensed in the condenser 9 may be recycled to the reactor 1 through the line 26 or recycled to the second distillation column 4 through the line 27. Moreover, the gas separated in the condenser 9 may be fed to the scrubber 10 through the line 13. Further, for the liquid component containing a predetermined amount of water, in the same manner as above, the liquid component may be separated into an aqueous phase and an oily phase, and these phases may be recycled. The lower boiling point fraction withdrawn from the second distillation column 4 is condensed by the condenser 9 to cool part of the reaction heat transferred from the reaction solution to the lower boiling point fraction through the flash vapor with the condenser 9.

(Reaction Step)

In the reaction step (carbonylation reaction step), methanol is carbonylated with carbon monoxide in the presence of the catalyst system. Incidentally, fresh methanol may be fed to the reaction system directly or indirectly, or methanol and/or a derivative thereof withdrawn from various distillation steps may be recycled and fed to the reaction system.

The catalyst system may usually comprise a metal catalyst, a co-catalyst, and an accelerator. Examples of the metal catalyst may include a transition metal catalyst, in particular, a metal catalyst containing the group 8 metal of the Periodic Table (e.g., a cobalt catalyst, a rhodium catalyst, and an iridium catalyst). The catalyst may be a metal as a simple substance or may be used in the form of an oxide (including a complex metal oxide), a hydroxide, a halide (e.g., a chloride, a bromide, and an iodide), a carboxylate (e.g., an acetate), a salt of an inorganic acid (e.g., a sulfate, a nitrate, and a phosphate), a complex, and others. These metal catalysts may be used alone or in combination. The preferred metal catalyst includes a rhodium catalyst and an iridium catalyst (particularly, a rhodium catalyst).

Moreover, it is preferred to use the metal catalyst in the form dissolvable in a reaction solution. Incidentally, since rhodium usually exists as a complex in the reaction solution, the form of the rhodium catalyst is not particularly limited to a specific one as long as the catalyst can change into a complex in the reaction solution, and may be used in various forms. As such a rhodium catalyst, a rhodium iodide complex [for example, $RhI_3$, $[RhI_2(CO)_4]^-$, and $[Rh(CO)_2I_2]^-$], a rhodium carbonyl complex, or the like is particularly preferred. Moreover, the catalyst may be stabilized in the reaction solution by addition of a halide salt (e.g., an iodide salt) and/or water.

The concentration of the metal catalyst is, for example, about 10 to 5000 ppm (on the basis of weight, the same applies hereinafter), preferably about 100 to 4000 ppm, more preferably about 200 to 3000 ppm, and particularly about 300 to 2000 ppm (e.g., about 500 to 1500 ppm) in the whole liquid phase in the reactor.

As the co-catalyst or the accelerator contained in the catalyst system, an ionic iodide (an iodide salt) is used. The iodide salt is added in order to stabilize the rhodium catalyst and inhibit side reactions, particularly, in a low water content. The iodide salt is not particularly limited to a specific one as far as the iodide salt produces an iodide ion in the reaction solution. The iodide salt may include, for example, a metal halide [for example, a metal iodide such as an alkali metal iodide (e.g., lithium iodide, sodium iodide, potassium iodide, rubidium iodide, and cesium iodide), an alkaline earth metal iodide (e.g., beryllium iodide, magnesium iodide, and calcium iodide), or an iodide of the group 38 metal of the Periodic Table (e.g., boron iodide and aluminum iodide)], an organic halide [for example, an organic iodide such as a phosphonium salt of an iodide (a phosphonium iodide) (e.g., a salt with tributylphosphine and triphenylphosphine) or an ammonium salt of an iodide (an ammonium iodide (e.g., a salt of tertiary amine, a pyridine compound, an imidazole compound, an imide compound, or the like with an iodide), a bromide corresponding to the iodide, and a chloride corresponding to the iodide]. Incidentally, the alkali metal iodide (e.g., lithium iodide) also functions as a stabilizer for the carbonylation catalyst (e.g., a rhodium catalyst). These iodide salts may be used alone or in combination. Among these iodide salts, an alkali metal iodide (such as lithium iodide) is preferred.

In the reactor (liquid reaction mixture), the concentration of the ionic iodide is, for example, about 1 to 25% by weight, preferably about 2 to 22% by weight, and more preferably about 3 to 20% by weight in whole liquid phase (or liquid reaction mixture) in the reactor. Further, the concentration of the iodide ion in the reactor may for example be about 0.07 to 2.5 mol/liter and preferably about 0.25 to 1.5 mol/liter.

As the accelerator contained in the catalyst system, an alkyl iodide (e.g., a $C_{1-4}$alkyl iodide such as methyl iodide, ethyl iodide, or propyl iodide), particularly methyl iodide, is utilized. Thus the accelerator may contain at least methyl iodide. Since the reaction is promoted at higher concentrations of the accelerator, an economically advantageous concentration can suitably be selected in consideration of the recovery of the accelerator, the plant size of a step for circulating the recovered accelerator to the reactor, the amount of energy necessary for the recovery or circulation, and others. In the reaction system, the concentration of the alkyl iodide (particularly methyl iodide) is, for example, about 1 to 25% by weight, preferably about 5 to 20% by weight, and more preferably about 6 to 16% by weight (e.g., about 12 to 15% by weight) in the whole liquid phase in the reactor.

The reaction is a continuous reaction, and the reaction solution may usually contain methyl acetate. The proportion of methyl acetate may be about 0.1 to 30% by weight, preferably about 0.3 to 20% by weight, and more preferably about 0.5 to 10% by weight (e.g., about 0.5 to 6% by weight) in whole reaction solution.

The carbon monoxide to be fed to the reaction system may be used as a pure gas or may be used as a gas diluted with an inactive gas (e.g., nitrogen, helium, and carbon dioxide). Moreover, exhausted gas component(s) containing carbon monoxide obtained from the succeeding step(s) may be recycled to the reaction system. The carbon monoxide partial pressure in the reactor may for example be about 2 to 30 atmospheres and preferably about 4 to 15 atmospheres.

In the carbonylation reaction, hydrogen is formed (or generated) by a shift reaction between carbon monoxide and water. Hydrogen may be fed to the reaction system. The hydrogen may be fed as a mixed gas with carbon monoxide as a raw material to the reaction system. Moreover, the hydrogen may be fed to the reaction system by recycling gaseous component(s) (including hydrogen, carbon monoxide, and others) exhausted in the succeeding distillation step(s) (distillation column), if necessary after suitably purifying the gaseous component(s). The hydrogen partial pressure in the reaction system may for example be about 0.5 to 200 kPa, preferably about 1 to 150 kPa, and more preferably about 5 to 100 kPa (e.g., about 10 to 50 kPa) in terms of absolute pressure.

The carbon monoxide partial pressure or hydrogen partial pressure in the reaction system may be adjusted, for example, by suitably adjusting the amount of the carbon monoxide and hydrogen fed and/or recycled to the reaction system, the amount of raw substances (e.g., methanol) fed to the reaction system, the reaction temperature, the reaction pressure, and others.

In the carbonylation reaction, the reaction temperature may be, for example, about 150 to 250° C., preferably about 160 to 230° C., and more preferably about 180 to 220° C. Moreover, the reaction pressure (total reactor pressure) may be, for example, about 15 to 40 atmospheres.

The reaction may be carried out in the presence or absence of a solvent. The reaction solvent is not limited to a specific one as long as the reactivity, or the separation or purification efficiency does not decrease, and a variety of solvents may be used. In usual cases, acetic acid as a product may be practically utilized as a solvent.

The concentration of water in the reaction system is not limited to a specific one, and may be a low concentration. The concentration of water in the reaction system is, for example, not more than 15% by weight (e.g., about 0.1 to 12% by weight), preferably not more than 10% by weight (e.g., about 0.1 to 6% by weight), and more preferably about 0.1 to 5% by weight and may usually be about 1 to 15% by weight (e.g., about 2 to 10% by weight) in the whole liquid-phase of the reaction system. The solubility of carbon monoxide in the solution fed to the flasher is decreased by carrying out the reaction while maintaining a specified concentration of each component [particularly, an iodide salt (lithium iodide) and water] in the reaction system, and the loss of carbon monoxide can be reduced.

In the foregoing carbonylation reaction, production of acetic acid is accompanied by production of an ester of the produced acetic acid with methanol (methyl acetate), water generated with the esterification reaction, additionally acetaldehyde, propionic acid, and others.

In the reaction system, generation of aldehydes may be depressed or inhibited by removing the aldehyde in the recycling stream from the succeeding step (s) (e.g., distillation column), or by modifying the reaction conditions, for example, reducing the proportion of the co-catalyst such as an alkyl iodide and/or the hydrogen partial pressure. Moreover, the generation of hydrogen in the reaction system may be depressed or inhibited by adjusting the concentration of water.

The space time yield of the objective acetic acid in the reaction system may be, for example, about 5 mol/Lh to 50 mol/Lh, preferably about 8 mol/Lh to 40 mol/Lh, and more preferably about 10 mol/Lh to 30 mol/Lh.

The vapor component withdrawn from the top of the reactor for the purpose of the pressure control of the reactor or others is preferably cooled with a condenser, a heat exchanger or other means to remove part of the reaction heat. It is preferable that the cooled vapor component be separated into a liquid component (containing acetic acid, methyl acetate, methyl iodide, acetaldehyde, water, and others) and a gaseous component (containing carbon monoxide, hydrogen, and others), the liquid component be recycled to the reactor and the gaseous component be introduced into the scrubber system.

Moreover, the reaction system (or the reaction mixture) may also contain methanol (unreacted methanol). The concentration of methanol in the reaction system may for example be not more than 1% by weight (e.g., about 0 to 0.8% by weight), preferably not more than 0.5% by weight (e.g., about 0 to 0.3% by weight), more preferably not more than 0.3% by weight (e.g., about 0 to 0.2% by weight), and usually not more than the detection limit (less than 0.1% by weight). Incidentally, the concentration of methyl acetate also depends on the concentration of methanol existing in the system. Thus the amount of methanol to be fed to the reaction system may be adjusted in association with the after-mentioned concentration of methyl acetate in the flasher.

(Flash Distillation Step or Catalyst Separation Step)

In the flash distillation step (flasher), from the reaction mixture fed from the reaction step or the reactor to the flasher (evaporator or flash evaporator), a low-volatile component or liquid catalyst mixture (a higher boiling point fraction) containing at least a higher boiling point catalyst component (a metal catalyst component, e.g., a rhodium catalyst and an ionic iodide salt) is separated as a liquid (component), and a volatile component or volatile phase (a lower boiling point fraction) containing acetic acid is separated as a vapor (component).

In the flash distillation step (flash evaporation step), the reaction mixture may be separated into the vapor component (or vaporized stream) and the liquid component (or liquid stream) with or without heating. For example, in adiabatic flash, the reaction mixture may be separated into the vapor component and the liquid component without heating and with reduced pressure, and in thermostatic flash, the reaction mixture may be separated into the vapor component and the liquid component with heating (and reduced pressure). The reaction mixture may be separated into the vapor component and the liquid component by combining these flash conditions.

In the flash distillation, the distillation temperature (or reaction temperature) may for example be about 100 to 260° C. (e.g., about 110 to 250° C.), preferably about 120 to 240° C. (e.g., about 140 to 230° C.), more preferably about 150 to 220° C. (e.g., about 160 to 210° C.), and particularly about 170 to 200° C. Moreover, in the flash distillation, the temperature of the liquid catalyst mixture (or the liquid temperature of the reaction mixture) may for example be about 80 to 200° C. (e.g., about 90 to 180° C.), preferably about 100 to 170° C. (e.g., about 120 to 160° C.), and more preferably about 130 to 160° C. Further, in the flash distillation, the absolute pressure may be about 0.03 to 1 MPa (e.g., about 0.05 to 1 MPa), preferably about 0.07 to 0.7 MPa, and more preferably about 0.1 to 0.5 MPa (e.g., about 0.15 to 0.4 MPa). Hydrogen iodide is easily produced (or the concentration of hydrogen iodide tends to increase) under such a relatively high temperature (and high pressure) condition. According to the present invention, however, even under such a condition, the production or increased concentration of hydrogen iodide in the flash evaporator can efficiently be inhibited.

The separation (flash distillation) of the metal catalyst component may usually be carried out with the use of a distillation column (a flash evaporator). Moreover, the metal catalyst component may be separated by means of flash distillation in combination with a mist-collecting method or a solid-collecting method which is widely used in industrial application.

The material of (or for forming) the flasher is not particularly limited to a specific one and may be a metal, a ceramic, a glass, or others. Practically, a flasher made of a metal is used. In particular, the concentration of hydrogen iodide in the inside of the flash evaporator can significantly be inhibited, and the corrosion of the flash evaporator can also be inhibited at a high level. Thus, as a flash evaporator in the present invention, there may be used not only a flash evaporator made of an expensive material having a high corrosion resistance (such as zirconium) but also a flash evaporator made of a relatively inexpensive material having not a very high corrosion resistance, for example, a metal as a simple substance (such as titanium or aluminum) and an alloy [for example, a transition-metal-based alloy such as an iron-based alloy (or an alloy containing iron as a main component, e.g., a stainless steel (including a stainless steel containing chromium, nickel, molybdenum and others)), a nickel-based alloy (or an alloy containing nickel as a main component, e.g., HASTELLOY (brand name) and INCONEL (brand name)), a cobalt-based alloy (or an alloy containing cobalt as a main component), or a titanium alloy; and an aluminum alloy].

The separation step of the liquid catalyst mixture may be composed of a single step, or may be composed of a plurality of steps in combination. The liquid catalyst mixture or higher boiling point catalyst component (metal catalyst component) separated by such step(s) may usually be recycled to the reaction system, as shown in the embodiment of the FIGURE. Moreover, the liquid catalyst mixture may be cooled (or heat-removed) by the heat exchanger and recycled to the reactor, as shown in the example of the FIGURE. The cooling can improve the heat removal efficiency of the whole system.

The separated liquid catalyst mixture (or low-volatile component or higher boiling point fraction) contains the metal catalyst (e.g., a rhodium catalyst), the ionic iodide (e.g., an alkali metal iodide such as lithium iodide), and in addition, components remaining without evaporation (e.g., acetic acid, methyl iodide, water, methyl acetate, and hydrogen iodide).

In the flash distillation (or flash evaporator), the ratio (weight ratio) of the volatile component to be separated relative to the liquid catalyst mixture (or low-volatile component) may be about 10/90 to 50/50, preferably about 15/85 to 40/60, and more preferably about 20/80 to 35/65 in a ratio of the former/the latter.

According to the present invention, among the components in the liquid catalyst mixture, the concentration of methyl acetate may be adjusted (or regulated). The adjustment of the concentration allows the production or increased concentration of hydrogen iodide in the flash evaporator to be inhibited efficiently in a wide range of flash distillation conditions. Multiple factors are involved in the reason why the increase in concentration of hydrogen iodide is prevented by adjusting the concentration of methyl acetate, and one of the factors includes consumption of hydrogen iodide by the following equilibrium reaction.

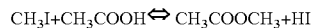

$$CH_3I + CH_3COOH \rightleftharpoons CH_3COOCH_3 + HI$$

The concentration of methyl acetate in the liquid catalyst mixture may be selected from the range of not less than 0.05% by weight (e.g., 0.1 to 20% by weight), and may for example be not less than 0.2% by weight (e.g., about 0.3 to 15% by weight), preferably not less than 0.5% by weight (e.g., about 0.6 to 10% by weight), and usually about 0.8 to 5% by weight (e.g., 1 to 4% by weight). In particular, the concentration of methyl acetate in the liquid catalyst mixture may be not less than 0.6% by weight (e.g., about 0.6 to 20% by weight), preferably not less than 0.7% by weight (e.g., about 0.7 to 15% by weight), more preferably not less than 0.8% by weight (e.g., about 0.8 to 10% by weight), and usually about 0.7 to 5% by weight (e.g., about 0.7 to 3% by weight, preferably about 0.8 to 2% by weight, and more preferably about 0.9 to 1.5% by weight). The concentration of methyl acetate is adjusted to the range, so that the production or increased concentration of hydrogen iodide can further efficiently be inhibited.

The concentration of water in the liquid catalyst mixture may for example be selected from the range of not more than 15% by weight (e.g., 0.1 to 12% by weight), and may for example be not more than 10% by weight (e.g., about 0.5 to 10% by weight), preferably not more than 8% by weight (e.g., about 0.8 to 8% by weight), and more preferably not more than 5% by weight (e.g., about 1 to 4% by weight).

Moreover, the concentration of acetic acid in the liquid catalyst mixture may for example be not less than 30% by weight (e.g., about 35 to 95% by weight), preferably not less than 40% by weight (e.g., about 45 to 90% by weight), and more preferably not less than 50% by weight (e.g., about 50 to 85% by weight) and may usually be about 60 to 90% by weight (e.g., about 70 to 90% by weight, and preferably about 75 to 85% by weight).

Further, the concentration of methyl iodide in the liquid catalyst mixture may be selected from the range of not more than 10% by weight (e.g., 0.001 to 8% by weight), and may for example be not more than 7% by weight (e.g., about 0.005 to 6% by weight), preferably not more than 5% by weight (e.g., about 0.01 to 4% by weight), more preferably not more than 3% by weight (e.g., about 0.05 to 2.5% by weight), particularly not more than 2% by weight (e.g., about 0.1 to 1.8% by weight) and may usually be about 0.1 to 3% by weight (e.g., about 0.3 to 2.5% by weight, preferably about 0.5 to 2% by weight, and more preferably about 1 to 1.5% by weight).

Furthermore, the concentration of the ionic iodide in the liquid catalyst mixture may for example be not more than 60% by weight (e.g., about 1 to 55% by weight), preferably not more than 50% by weight (e.g., about 2 to 45% by weight), more preferably not more than 40% by weight (e.g., about 3 to 37% by weight), and particularly not more than 36% by weight (e.g., about 5 to 35% by weight). Multiple factors are also involved in the reason why the increase in concentration of hydrogen iodide is prevented by adjusting the concentration of the ionic iodide, and one of the factors includes consumption of hydrogen iodide by the following equilibrium reaction. Incidentally, the same equilibrium reaction also applies to hydrogen iodide in the reaction mixture.

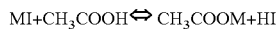

$$MI + CH_3COOH \Leftrightarrow CH_3COOM + HI$$

[In the formula, M represents a residue of an ionic iodide (or cationic group, e.g., an alkali metal such as lithium)]

Incidentally, the concentration of the metal catalyst in the liquid catalyst mixture may for example be not less than 100 ppm (e.g., about 150 to 10000 ppm), preferably not less than 200 ppm (e.g., about 250 to 5000 ppm), and more preferably not less than 300 ppm (e.g., about 350 to 3000 ppm) on the basis of weight.

Moreover, the concentration of methanol in the liquid catalyst mixture may for example be not more than 1% by weight (e.g., about 0 to 0.8% by weight), preferably not more than 0.5% by weight (e.g., about 0 to 0.3% by weight), and more preferably not more than 0.3% by weight (e.g., about 0 to 0.2% by weight). As described later, as the concentration of methanol is higher, the concentration of methyl acetate in the liquid catalyst mixture is easily and efficiently increased.

For example, the concentration of methyl acetate in the liquid catalyst mixture can efficiently be increased by increasing the concentration of methanol in the reaction mixture (or liquid catalyst mixture). That is, as represented by the following formula, methanol is allowed to react with acetic acid to produce methyl acetate (equilibrium reaction). Thus the production reaction of methyl acetate easily occurs as the concentration of methanol increases. As a result, the concentration of methyl acetate in the liquid catalyst mixture can be increased. Incidentally, the same equilibrium reaction also applies to hydrogen iodide in the reaction mixture.

$$CH_3OH + CH_3COOH \Leftrightarrow CH_3COOOCH_3 + H_2O$$

In the range that the production efficiency of acetic acid is ensured sufficiently, the concentration of methanol can be increased by increasing the concentration of methanol to be fed in the reaction or by decreasing the reaction rate to inhibit consumption of methanol. The reaction rate can be adjusted by suitably selecting the reaction temperature, the concentration of the catalyst (e.g., the concentration of methyl iodide and the concentration of the metal catalyst), the concentration of carbon monoxide (or carbon monoxide partial pressure), and others. The concentration of methanol may be adjusted by adding methanol directly, as described later.

Moreover, the concentration of methyl acetate in the liquid catalyst mixture may be adjusted by adding methyl acetate and/or a component for producing methyl acetate (e.g., methanol and dimethyl ether). Incidentally, as described above, methanol is allowed to react with acetic acid to produce methyl acetate; and dimethyl ether is allowed to react with hydrogen iodide or others to give methanol, which is allowed to react with acetic acid to produce methyl acetate. If necessary, a component for increasing or decreasing the concentration of each component may be added or mixed in the form of a mixture containing a solvent.

When the increasing or decreasing component is added to the reaction mixture, the position (or timing) of addition is not particularly limited to a specific one as far as the increasing or decreasing component is added before the reaction mixture is fed to the flash evaporator. The increasing or decreasing component may be fed to the reactor. In terms of process efficiency, the increasing or decreasing component may be fed to the reaction mixture after the reaction mixture is discharged from the reactor and before the reaction mixture is fed to the flash evaporator (for example, as shown in the FIGURE, the increasing or decreasing component may be fed to a line for feeding the flash evaporator with the reaction mixture discharged from the reactor).

Moreover, when the increasing or decreasing component is added to the flash evaporator (or the increasing or decreasing component is mixed to the reaction mixture in the flash evaporator), the position (height level) of addition is not particularly limited to a specific one. The increasing or decreasing component may be added to either the liquid phase portion or the gaseous phase portion in the flash evaporator, or both. The increasing or decreasing component may be added to the process solution to be recycled from the succeeding step(s) to the flash evaporator.

The volatile component (acetic acid stream) separated in the flasher contains product acetic acid, in addition, methyl iodide, an ester of the product acetic acid with methanol (e.g., methyl acetate), water, a very small amount of by-product(s) (e.g., acetaldehyde and propionic acid) and others. The volatile component may be distilled in the first distillation column and the second distillation column to produce purified acetic acid.

As described above, the production or increased concentration of hydrogen iodide in the flasher can be inhibited. Thus the concentration of hydrogen iodide in the volatile component may for example be regulated to not more than 1% by weight (e.g., about 0 or detection limit to 8000 ppm), preferably not more than 5000 ppm (e.g., about 1 to 4000% by weight), and more preferably not more than 3000 ppm (e.g., about 10 to 2000% by weight). Moreover, the concentration of hydrogen iodide in the liquid catalyst mixture may for example be regulated to not more than 1% by weight (e.g., about 0 to 8000 ppm), preferably not more than 5000 ppm (e.g., about 1 to 4000 ppm), and more preferably not more than 3000 ppm (e.g., about 10 to 2000 ppm).

The concentration of hydrogen iodide may be measured directly or measured (or calculated) indirectly. For example, the concentration of the iodide ion derived from the iodide salt [for example, an iodide derived from the co-catalyst such as LiI, and a metal iodide (e.g., an iodide of a corroded metal (such as Fe, Ni, Cr, Mo, or Zn) produced in the process of the acetic acid production)] may be subtracted from the total concentration of iodide ions (I$^-$) to determine (or calculate) the concentration of hydrogen iodide.

Part of the separated volatile component (acetic acid stream) may be introduced into a condenser or a heat exchanger for cooling or heat-removal, as the embodiment illustrated in the FIGURE. Since the reaction heat transferred from the reaction solution to the flash vapor can partly be cooled by the heat removal, the heat removal efficiency can be improved, and acetic acid with a high purity can be produced without installing an external circulation cooling unit in the reactor. Moreover, the cooled volatile component may be recycled to the reaction system, as the embodiment illustrated in the FIGURE. On the other hand, the gaseous component in the cooled volatile component may be introduced into the scrubber system.

(Acetic Acid Collection Step)

In the acetic acid collection step (distillation step), the volatile component is fed to the first distillation column, a first lower boiling point component (a lower boiling point fraction containing methyl iodide, acetic acid, methyl acetate, by-product acetaldehyde, and others) is separated as an overhead (volatile component or vaporized component) from the volatile component by distillation (first distillation), and a stream mainly containing acetic acid is collected as a liquid component (first liquid component). The volatile component to be subjected to the first distillation may be a reaction mixture itself obtained from the reactor, and is usually a volatile component obtained by subjecting the reaction mixture to further flash distillation and separating the liquid catalyst mixture.

That is, the separated volatile component is fed to the first distillation column (splitter column) and separated into a lower boiling point fraction (overhead) containing a lower boiling point component and a stream containing acetic acid (acetic acid stream) by distillation.

All of the volatile component may be fed to the first distillation column, or as described above, part of the volatile component may be introduced into the heat exchanger and the remaining (residual) stream may be fed to the first distillation column. In the first distillation column, the first lower boiling point component (lower boiling point fraction) containing at least part of the lower boiling point component (e.g., methyl iodide, methyl acetate, acetaldehyde, and hydrogen iodide) is separated, and the lower boiling point fraction containing acetic acid is discharged as a liquid stream. Incidentally, in the first distillation column, as described in the embodiment of the FIGURE, each of the first lower boiling point component and the first higher boiling point component (higher boiling point fraction, bottom fraction) containing at least part of the higher boiling point component (such as propionic acid or water) may be separated. Moreover, in the embodiment of FIG. 1, the first liquid stream is withdrawn (or extracted or collected) as a side stream by side cut. The first liquid stream may be extracted from the bottom of the column or withdrawn (or collected) together with the higher boiling point fraction.

As described above, the acetic acid stream fed to the first distillation column is not limited to an acetic acid stream obtained by removing the rhodium catalyst component from the reaction mixture of the reaction system.

The acetic acid stream may contain at least acetic acid, the lower boiling point component, the higher boiling point component, and others (for example, may contain acetic acid, methyl acetate, methyl iodide, water, and hydrogen iodide); or simply may be a mixture of these components.

As the first distillation column, there may be used, for example, a conventional distillation column, e.g., a distillation column such as a plate column or a packed column. The material of (or forming) the first distillation column may include the same material as that of the flasher. As the first distillation column, there may be used a distillation column made of the same material, which is relatively inexpensive material (e.g., an alloy), as that of the flash evaporator.

The distillation temperature and pressure in the first distillation column may suitably be selected depending on the condition such as the species of the distillation column, or the main subject (target) for removal selected from the lower boiling point component and the higher boiling point component. For example, for the plate column, the inner pressure of the column (usually, the pressure of the column top) may be about 0.01 to 1 MPa, preferably about 0.01 to 0.7 MPa, and more preferably about 0.05 to 0.5 MPa in terms of gauge pressure.

Moreover, in the first distillation column, the inner temperature of the column (usually, the temperature of the column top) may be adjusted by adjusting the inner pressure of the column, and may be, for example, about 20 to 180° C., preferably about 50 to 150° C., and more preferably about 100 to 140° C.

Moreover, for the plate column, the theoretical number of plates is not particularly limited to a specific one, and, depending on the species of the component to be separated, is about 5 to 50, preferably about 7 to 35, and more preferably about 8 to 30. Further, in order to separate acetaldehyde highly (or with a high precision) in the first distillation column, the theoretical number of plates may be about 10 to 80, preferably about 12 to 60, and more preferably about 15 to 40.

In the first distillation column, the reflux ratio may be selected from, for example, about 0.5 to 3,000, and preferably about 0.8 to 2,000 depending on the above-mentioned theoretical number of plates, or may be reduced by increasing the theoretical number of plates. Incidentally, in the first distillation column, the distillation may be carried out without reflux.

Since the lower boiling point fraction (first lower boiling point component) separated from the first distillation column contains a useful component (e.g., methyl iodide and methyl acetate), the lower boiling point fraction may directly be recycled to the reaction system (or reactor) and/or the first distillation column, or may be liquefied by heat-removing part of the reaction heat in the reaction system (e.g., the reactor) using a condenser, a heat exchanger, or other means and then recycled to the reactor and/or the first distillation column. For example, the lower boiling point fraction withdrawn from the first distillation column is not necessary recycled to the first distillation column after condensation by the condenser as the embodiment of FIG. 1. The withdrawn lower boiling point fraction may directly be recycled, or simply cooled to remove an offgas component (e.g., carbon monoxide and hydrogen) and then the remaining (residual) liquid component may be recycled. Moreover, among lower boiling point components in the lower boiling point fraction, acetaldehyde deteriorates the quality of acetic acid as a final product. Thus, if necessary, after removing acetaldehyde (e.g., after removing acetaldehyde by subjecting the fraction containing the lower boiling point impurities to the after-mentioned acetaldehyde separation step (acetaldehyde-separating column)), the remaining component(s) may be recycled to the reaction system and/or the first distillation column. Incidentally, the offgas component may be introduced into the scrubber system.

The higher boiling point fraction (bottom fraction) separated in the first distillation column contains water, acetic acid, an entrained rhodium catalyst, lithium iodide, in addition, acetic acid remaining without being evaporated, the lower boiling point impurities, and others. Thus, if necessary, the higher boiling point fraction may be recycled to the reaction system (reactor) and/or the flasher. Incidentally, prior to recycling, propionic acid, which deteriorates the quality of acetic acid as a final product, may be removed off.

(Acetic Acid Purification Step)

In the acetic acid purification step, hydrogen iodide, a lower boiling point component, and a higher boiling point component, each of which remains without being separated in the first distillation column, are removed from the first liquid stream by distillation with further high precision, and purified acetic acid is collected. That is, in the acetic acid purification step, the first liquid stream is fed to the second distillation column, and the second lower boiling point component is further separated as an overhead, and the second liquid stream containing acetic acid is collected.

The first liquid stream separated or collected in the first distillation column and fed to the second distillation column is a liquid composition mainly containing acetic acid. The first liquid stream contains other components (e.g., methyl iodide, methyl acetate, water, and hydrogen iodide) in addition to acetic acid. In the first liquid stream, the concentrations of these other components may be selected depending on the adjustment or nonadjustment of the concentration of each component in the flash evaporator, the distillation conditions in the first distillation column, and others.

For example, the concentration of methyl iodide in the first liquid stream may be about 0 to 10% by weight (e.g., about 10 ppm to 8% by weight), preferably about 0.1 to 8% by weight, more preferably about 0.2 to 7% by weight, and particularly about 0.3 to 6% by weight (e.g., about 0.5 to 5% by weight, preferably about 0.7 to 4% by weight, and more preferably about 1 to 3% by weight) and may usually be not more than 4% by weight (e.g., about 0 to 4% by weight, preferably about 10 ppm to 3.5% by weight, more preferably about 1 to 3.3% by weight, and particularly about 1.5 to 3.2% by weight).

Incidentally, when the concentration of methyl iodide is low, the condensation hydrogen iodide derived from methyl iodide can be inhibited in the upper part of the second distillation column. Moreover, according to the present invention, even when the concentration of methyl iodide is high, the condensation of hydrogen iodide can be inhibited in the whole second distillation column.

Moreover, the concentration of methyl acetate in the first liquid stream may be about 0 to 10% by weight, preferably about 0.1 to 8% by weight, and more preferably about 0.2 to 7% by weight and may usually be about 0.2 to 6% by weight [e.g., about 0.3 to 5% by weight, preferably about 0.4 to 4% by weight, more preferably about 0.5 to 3% by weight, particularly about 0.7 to 2.5% by weight (e.g., about 1 to 2% by weight)].

Incidentally, when the concentration of methyl acetate is high, the condensation of hydrogen iodide is further easily inhibited in the upper part of the second distillation column probably due to the consumption of hydrogen iodide by the reaction of hydrogen iodide with methyl acetate. Moreover, according to the present invention, even when the concentration of methyl acetate is low, the condensation of hydrogen iodide can he inhibited in the whole second distillation column. The concentration of methyl acetate can efficiently be increased by adjusting the concentration of methyl acetate in the liquid catalyst mixture in the flash distillation, as described above. The concentration of methyl acetate in the first liquid stream may be increased by adding methyl acetate to the first distillation column.

Further, the concentration of water in the first liquid stream may be about 0.1 to 25% by weight, preferably about 0.2 to 20% by weight, more preferably about 0.3 to 15% by weight, and particularly about 0.5 to 12% by weight (e.g., about 0.7 to 10% by weight and preferably about 1 to 8% by weight) and may usually be less than 5% by weight [for example, not more than 4% by weight, e.g., about 0.1 to 4% by weight, preferably about 0.3 to 3.5% by weight, more preferably not more than 3% by weight (e.g., about 0.5 to 3% by weight), and particularly about 1 to 2.5% by weight (e.g., about 1 to 2% by weight)].

Incidentally, when the concentration of water is low, the condensation of hydrogen iodide can further easily be inhibited in the upper part of the second distillation column. In particular, as the concentration of water in the first liquid stream (or liquid object) and that of water in the column are lower, the corrosion rate of the second distillation column decreases. The corrosion rate can significantly decreases at a water concentration of less than 5% by weight, particularly less than 3% by weight. Thus the combination of the concentration of water with the after-mentioned adding manner of the alkali component can further efficiently inhibit the condensation of hydrogen iodide in the second distillation and the corrosion of the second distillation column. Moreover, according to the present invention, even when the concentration of water is high, the condensation of hydrogen iodide can be inhibited in the whole second distillation column. Incidentally, as described in Japanese Patent Application Laid-Open No. 2009-501129, the addition of water to the first distillation column sometimes increases the concentration of water in the first liquid stream.

The concentration of hydrogen iodide in the first liquid stream may for example be not more than 2000 ppm (e.g., about 0 to 1800 ppm), preferably not more than 1500 ppm (e.g., about 1 to 1200 ppm), more preferably not more than 1000 ppm (e.g., about 2 to 900 ppm), and usually not more than 800 ppm (e.g., about 3 to 700 ppm) on the basis of weight. For a relatively low concentration, the concentration of hydrogen iodide in the first liquid component may be not more than 500 ppm (e.g., about 0 to 300 ppm), preferably not more than 100 ppm (e.g., about 0.1 to 50 ppm), more preferably not more than 30 ppm (e.g., about 0.3 to 25 ppm), and usually about 1 to 30 ppm (e.g., about 2 to 25 ppm) on the basis of weight. If necessary, the concentration of hydrogen iodide in the first liquid component may be decreased by using the method described in Japanese Patent Application Laid-Open No. 2009-501129 or other methods.

Incidentally, the concentration of acetic acid in the first liquid stream may for example be not less than 50% by weight (e.g., about 55 to 99.5% by weight), preferably not less than 60% by weight (e.g., about 65 to 99% by weight), more preferably not less than 70% by weight (e.g., about 75 to 98.5% by weight), and particularly not less than 80% by weight (e.g., about 85 to 98% by weight) and usually be about 80 to 99.5% by weight (e.g., about 85 to 99% by weight, preferably about 90 to 98% by weight, and more preferably about 92 to 97% by weight).

In this manner, the first liquid stream contains hydrogen iodide or a component producing hydrogen iodide in the second distillation column. When the first liquid stream is directly subjected to the second distillation, hydrogen iodide is condensed through continuous reactions in the second distillation column (in particular, the upper part or gaseous phase portion of the distillation column). Thus according to the present invention, the alkali component is added (or fed or mixed) to the first liquid stream in the following manners or embodiments (1) and/or (2), and the liquid object containing the first liquid stream and the alkali component is subjected to distillation in the second distillation column:

(1) the alkali component is added to or mixed with the first liquid stream before the first liquid stream is fed to the second distillation column, (2) in the second distillation column, the alkali component is added or mixed at the same height level (or same position or same plate) as a height level (or position or plate) at which the first liquid stream is fed or at a height level or position upper (or higher) than the height level (or position) at which the first liquid stream is fed.

In the manner (1), it is sufficient that the mixing position (adding position) of the alkali component to the first liquid stream is situated prior to feeding to the second distillation column (before feeding to the second distillation column). For example, the alkali component may be fed to a line for feeding the first liquid component from the first distillation column to the second distillation column. Incidentally, the alkali component is usually fed after the first liquid stream is discharged from the first distillation column.

Incidentally, in the manner (1), the time from when the first liquid component and the alkali component are mixed till when the mixture is fed to the second distillation column (retention time, contact time) may be not more than 5 minutes (e.g., about 1 second to 4 minutes), preferably not more than 4 minutes (e.g., about 3 seconds to 3 minutes), more preferably not more than 3 minutes (e.g., about 5 seconds to 2 minutes). When the retention time is too long, the alkali component is consumed by methyl iodide in the first liquid stream, so that the selective neutralization of hydrogen iodide sometimes decreases.

Moreover, in the manner (2), it is sufficient that the alkali component is added at the same position as a position at which the first liquid stream is fed to the second distillation column or at a position upper than the position at which the first liquid stream is fed to the second distillation column. When the adding position of the alkali component is upper than the adding position of the first liquid stream, for example, in the second distillation column, the plate to which the alkali component is added may be the first or higher plate (e.g., the first to the 30th plate, preferably the first to the 20th plate, and more preferably the first to the 10th plate) above the plate to which the first liquid stream is fed. Incidentally, the adding position of the first liquid stream is usually situated at a position upper or higher than the position for collecting the second liquid stream (e.g., by side cut).

The contact temperature of the first liquid component and the alkali component [the temperature (liquid temperature) of the liquid object containing the first liquid component and the alkali component] may for example be about 50 to 190° C., preferably about 70 to 180° C. (e.g., about 90 to 175° C.), and more preferably about 100 to 170° C. In particular, the above range of the liquid temperature is combined with the manner (1) to achieve efficient progress of neutralization of hydrogen iodide (HI) and the alkali component while inhibiting the consumption of the alkali component by methyl iodide in the first liquid stream.

The alkali component may include a metal hydroxide [for example, an alkali metal hydroxide (e.g., lithium hydroxide, sodium hydroxide, and potassium hydroxide), an alkaline earth metal hydroxide (e.g., calcium hydroxide), and hydroxides of the group 3 to 12 metals of the Periodic Table (e.g., iron (II) hydroxide, zinc hydroxide, and copper (II) hydroxide)], a metal oxide [for example, a metal oxide corresponding to the metal hydroxide, such as an alkali metal oxide (e.g., sodium oxide)], a salt of an inorganic acid (for example, a metal salt of a weak acid, such as an alkali metal carbonate or an alkali metal bicarbonate (hydrogen carbonate)), a salt of an organic acid [for example, a acetate salt such as a metal salt of acetic acid (e.g., an alkali metal acetate such as lithium acetate, potassium acetate, or sodium acetate; an alkaline earth metal acetate such as calcium acetate; or a salt of acetic acid with any one of the group 3 to 12 metals of the Periodic Table, such as iron (II) acetate, zinc acetate, or copper (II) acetate)], an amine, ammonia, and others. The alkali components may be used alone or in combination.

Among them, the preferred alkali component includes an alkali metal hydroxide, an alkaline earth metal hydroxide, an acetate salt (e.g., an alkali metal acetate salt, an alkaline earth metal acetate salt), particularly an alkali metal hydroxide.

The amount to be added of the alkali component may suitably be selected depending on the liquid composition (of formulation) of the first liquid stream. For example, the concentration of the alkali component in the liquid object (or the proportion of the alkali component in the total amount of the first liquid stream and the alkali component) may be selected from the range of not more than 100000 ppm (e.g., about 1 to 70000 ppm) on the basis of weight, and the alkali component may be added to the first liquid stream so that the concentration of the alkali component may be not more than 50000 ppm (e.g., about 3 to 30000 ppm), preferably not more than 20000 ppm (e.g., about 5 to 15000 ppm), and more preferably not more than 10000 ppm (e.g., about 10 to 7000 ppm). In particular, the alkali component may be added to the first liquid stream so that the concentration of the alkali component in the liquid object may be not more than 5000 ppm (e.g., about 1 to 3000 ppm), preferably not more than 2000 ppm (e.g., about 5 to 1500 ppm), and more preferably not more than 1000 ppm (e.g., 10 to 900 ppm) on the basis of weight or so that the concentration of the alkali component may be not more than 800 ppm [for example, about 5 to 750 ppm, preferably not more than 500 ppm (e.g., about 10 to 400 ppm)], usually about 10 to 1500 ppm (e.g., preferably about 20 to 1200 ppm, more preferably about 30 to 1000 ppm, and particularly about 40 to 800 ppm) on the basis of weight.

Moreover, the amount to be added of the alkali component relative to 1 mol of hydrogen iodide in the first liquid stream (or the liquid object to be treated) may be selected form the range of not less than 1 molar equivalent and may for example be about 1 to 2000 molar equivalents (e.g., about 1.5 to 1500 molar equivalents), preferably about 2 to 1000 molar equivalents (e.g., about 2.5 to 800 molar equivalents), more preferably about 3 to 600 molar equivalents (e.g., about 5 to 500 molar equivalent), and particularly about 10 to 300 molar equivalents. In particular, the amount to be added of the alkali component relative to 1 mol of hydrogen iodide in the first liquid stream (or the liquid object to be treated) may be not more than 200 molar equivalents (e.g., about 1 to 150 molar equivalents), preferably not more than 100 molar equivalents (e.g., about 1.5 to 90 molar equivalents), more preferably not more than 85 molar equivalents (e.g., about 2 to 83 molar equivalents), and particularly not more than 80 molar equivalents (e.g., about 3 to 78 molar equivalents) and may usually be about 1 to 85 molar equivalents (e.g., about 1 to 82 molar equivalents, preferably about 3 to 80 molar equivalents, and more preferably about 5 to 78 molar equivalents).

According to the present invention, even if the amount of the alkali component is small, sufficiently effective removal of hydrogen iodide (HI) can be achieved. Incidentally, an unconsumed alkali component (e.g., an alkali metal hydroxide) is accumulated in the lower part of the second distillation column and finally withdrawn from the bottom or others of the second distillation column. Accordingly, when the alkali component is accumulated in a large quantity, it is necessary to withdraw a large quantity of the bottom fraction containing acetic acid in order to avoid the alkali component from being mixed in purified acetic acid. Moreover, the alkali component is accumulated in a large quantity, the entrainment of the alkali component causes an increase in concentration of a component (e.g., a potassium component) derived from the alkali component in purified acetic acid, or the corrosion of the distillation column tends to accelerate due to an elevation of the boiling point. Further, when the temperature of the second distillation column is a room temperature, the alkali component is sometimes solidified (or crystallized) due to the saturation, thereby deteriorating handling properties. Therefore, the process of present invention, in which a small amount of the alkali component is allowed to react with hydrogen iodide, is extremely advantageous in terms of process efficiency.

According to the present invention, the second distillation may be performed in the presence of the component (A) which has a relatively low boiling point and is capable of consuming hydrogen iodide by a reaction with hydrogen iodide (equilibrium reaction) or inhibiting production of hydrogen iodide in the equilibrium reaction (for example, inhibiting a reaction of methyl iodide with water). The second distillation in the presence of the component (A) in combination with the alkali component can inhibit the condensation of hydrogen iodide in the upper part of the second distillation column at a further high level. Incidentally, as the component (A), a component having a boiling point lower than the boiling point of acetic acid (that is, lower than 118° C.) is practically used in terms of the separability from purified acetic acid or the decrease in concentration of hydrogen iodide in the upper part of the distillation column.

The component (A) may include an alcohol (for example, a $C_{1-4}$alkanol such as methanol, ethanol, propanol, isopropanol, or 2-butanol), an ether (for example, a $diC_{1-3}$alkyl ether such as dimethyl ether, methyl ethyl ether, diethyl ether, dipropyl ether, or diisopropyl ether), and an acetate ester [for example, an alkyl acetate (e.g., an $C_{1-3}$alkyl acetate such as methyl acetate, ethyl acetate, propyl acetate, or isopropyl acetate)]. These components (A) may be used alone or in combination.

The preferred component (A) may include methanol, dimethyl ether, methyl acetate, and others.

The concentration of the component (A) in the liquid object may be selected from the range of not less than 0.1% by weight (e.g., about 0.15 to 15% by weight) and may for example be not less than 0.2% by weight (e.g., about 0.25 to 12% by weight), preferably not less than 0.3% by weight (e.g., about 0.35 to 10% by weight), more preferably not less than 0.4% by weight (e.g., about 0.45 to 8% by weight), particularly not less than 1% by weight (e.g., about 1 to 5% by weight), and usually not less than 0.5% by weight [e.g., about 0.6 to 10% by weight, preferably about 0.7 to 8% by weight, more preferably about 0.8 to 6% by weight (e.g., about 1 to 4% by weight), and particularly about 1 to 2% by weight].

Incidentally, in the gaseous phase (or gaseous phase portion or column top portion) of the inside of the second distillation column, the concentration of the component (A) may be not less than 1% by weight (e.g., about 1.5 to 20% by weight), preferably not less than 2% by weight (e.g., about 2.5 to 15% by weight), and more preferably not less than 3% by weight (e.g., about 3 to 12% by weight).

Moreover, in the gaseous phase of the inside of the second distillation column, the ratio of methyl iodide relative to the component (A) [the former/the latter] (weight ratio) may be about 0.01 to 10 and preferably about 0.1 to 5.

The component (A) may be contained in the first liquid stream (for example, the case where a sufficient concentration of methyl acetate is contained in the first liquid stream), or may be added newly (or specially). That is, the component (A) may be added to the first liquid stream (or second distillation column). The manner for adding (or mixing) the component (A) is not particularly limited to a specific one as far as the component (A) is allowed to exist in the liquid object in the second distillation column, and may be the following manners (a) and/or (b):

(a) the component (A) is added or mixed to the first liquid stream before the first liquid stream is fed to the second distillation column, (b) the component (A) is added or mixed to the first liquid stream in the second distillation column.

In the manner (b), as is the case with the alkali component, in the second distillation column, the component (A) may be added or mixed at the same position (or same plate) as a position (or plate) at which the first liquid stream is fed or at a position (or plate) upper than the position at which the first liquid stream is fed. In particular, it is preferable that the component (A) be fed at the same position as a position at which the first liquid stream is fed (a plate to be fed or supplied) or at a position (or plate) upper than (e.g., the first plate above) the position at which the first liquid stream is fed (the plate to be fed or supplied). Moreover, the component (A) may be added together with the alkali component, or the component (A) and the alkali component may be added separately.

Incidentally, with respect to the component (A), the time (retention time, contact time) from when the first liquid component and the component (A) are mixed till when the mixture is fed to the second distillation column may for example be not less than 1 second (e.g., about 2 seconds to 20 minutes), preferably not less than 5 seconds (e.g., about 5 seconds to 15 minutes), more preferably about 10 seconds to 10 minutes (e.g., about 20 seconds to 7 minutes) and may usually be about 10 seconds to 5 minutes [for example, about 10 seconds to 3 minutes (e.g., about 10 seconds to 1 minute)]. Moreover, the contact temperature of the first liquid component and the component (A) [the temperature (liquid temperature) of the liquid object containing the first liquid component and the component (A)] may for example be about 20 to 190° C., preferably about 50 to 180° C. (e.g., about 70 to 175° C.), and more preferably about 100 to 170° C. Probably because the retention time or the liquid temperature within the above-mentioned range accelerates the reaction of the component (A) with hydrogen iodide or the progress of the reaction in the second distillation column to some extent, the increase in concentration of hydrogen iodide in the second distillation column tends to be inhibited further efficiently.

As the second distillation column, there may be used a conventional distillation column, for example, a plate column, a packed column, and other columns. The material of (or forming) the second distillation column may include the same material as that of the first distillation column. According to the present invention, since the condensation of hydrogen iodide in the inside of the second distillation column can significantly inhibited, there may be used not only a distillation column made of an expensive material having a high corrosion resistance (such as zirconium) but also a distillation column made of a relatively inexpensive material having not a very high corrosion resistance, for example, an alloy [for example, a transition-metal-based alloy such as an iron-based alloy (or an alloy containing iron as a main component, e.g., a stainless steel (including a stainless steel containing chromium, nickel, molybdenum and others)), a nickel-based alloy (or an alloy containing nickel as a main component, e.g., HASTELLOY (brand name) and INCONEL (brand name)), a cobalt-based alloy (or an alloy containing cobalt as a main component)]. Among others, an iron-based alloy or a nickel-based alloy is preferred.

The distillation temperature and pressure in the second distillation column may suitably be selected depending on the condition such as the species of the distillation column, or the main subject (target) for removal selected from the lower boiling point component and the higher boiling point component. For example, the inner pressure of the column (usually, the pressure of the column top) may be about 0.01 to 1 MPa, preferably about 0.01 to 0.7 MPa, and more preferably about 0.05 to 0.5 MPa in terms of gauge pressure.

In the second distillation column, the inner temperature of the column may for example be about 30 to 200° C., preferably about 80 to 180° C., and more preferably about 100 to 170° C. depending on the inner pressure of the column. The temperature of the column top (or the temperature of the gaseous phase) may for example be about 30 to 180° C., preferably about 50 to 150° C., and more preferably about 70 to 120° C. Further, the temperature of the column bottom may for example be about 80 to 200° C., preferably about 100 to 190° C. (e.g., about 120 to 185° C.), and more preferably about 130 to 180° C. (e.g., about 140 to 170° C.)

Moreover, the theoretical number of plates of the second distillation column is not particularly limited to a specific one, and, depending on the species of the component to be separated, may be about 5 to 1500, preferably about 10 to 120, and more preferably about 20 to 100 and may usually be about 30 to 120 (e.g., about 40 to 100). Further, in the second distillation column, the reflux ratio may be selected from, for example, about 0.1 to 100, preferably about 0.3 to 50, and more preferably about 0.5 to 30 (e.g., about 0.5 to 20) depending on the above-mentioned theoretical number of plates. Incidentally, in the first distillation column, the distillation may be carried out without reflux.

According to the present invention, as described above, the distillation in the presence of the alkali component (and the component (A)) can inhibit the increase in concentration of hydrogen iodide in the second distillation column. In particular, according to the present invention, the condensation of hydrogen iodide can significantly be inhibited even in the upper part (gaseous phase portion) of the second distillation column. For example, in the continuous reaction, the concentration of hydrogen iodide in the second lower boiling point component (distillate) is less than 40 ppm (e.g., about 0 or detection limit to 38 ppm), preferably not more than 36 ppm (e.g., about 0 or detection limit to 35 ppm), more preferably not more than 33 ppm (e.g., about 0 or detection limit to 32 ppm), and particularly not more than 30 ppm (e.g., about 0 or detection limit to 25 ppm).

Since the lower boiling point fraction (second lower boiling point component) separated from the second distillation column contains a useful component such as methyl iodide or methyl acetate, the lower boiling point fraction may directly be recycled to the reaction system (e.g., the reactor) and/or the second distillation column. In order to remove part of the reaction heat, as the same manner as the lower boiling point fraction withdrawn from the first distillation column, the lower boiling point fraction may be liquefied by a condenser, a heat exchanger, or other means and then recycled. Moreover, since the lower boiling point fraction sometimes contains acetaldehyde, the lower boiling point fraction may for example be recycled after removing acetaldehyde with the after-mentioned aldehyde-separating column, if necessary. Incidentally, the off gas component may be introduced into the scrubber system.

In the embodiment of FIG. 1, the purified acetic acid stream (second liquid stream) is withdrawn (or collected) by side cut, and the position of the side stream port may usually be at a middle or lower position of the second distillation column. As described above, usually, the side stream port for withdrawing the second liquid stream is practically situated at a position lower than the position (the position of the feed port) for feeding the first liquid stream.

Moreover, in the second distillation column, each of the second lower boiling point component and the second higher boiling point component (higher boiling point fraction, bottom fraction) containing at least part of the higher boiling point component (such as propionic acid or water) may be separated. Moreover, in the embodiment of FIG. 1, the second liquid stream is withdrawn (or extracted or collected) as a side stream by side cut. The second liquid stream may be extracted from the bottom of the column or withdrawn (or collected) together with the higher boiling point fraction (second higher boiling point component).

Incidentally, the second higher boiling point component may be discharged from the bottom or lower part of the column. Since the higher boiling point component separated from the second distillation column contains propionic acid, and others, the higher boiling point fraction may directly be discarded (or removed off). Moreover, since the second higher boiling point component further sometimes contains acetic acid, if necessary, the higher boiling point fraction from which propionic acid is removed and/or recovered may be recycled to the reaction system (e.g., the reactor). Incidentally, by withdrawing the acetic acid stream (second liquid fraction) from the side stream port existing at an upper position relative to the bottom port for withdrawing the second higher boiling point component, the side stream and the higher boiling point component (higher boiling point fraction) may efficiently be separated.

(Iodide Removal Step)

The purified acetic acid (second liquid stream) recovered is usually introduced into a column for product acetic acid and obtained as product acetic acid. Prior or posterior to introduction into the column for product acetic acid, the purified acetic acid may further be subjected to an iodide-removing step to remove an iodide (e.g., a $C_{1-15}$alkyl iodide such as hexyl iodide or decyl iodide).

In the iodide removal step (or iodide-removing step), the acetic acid stream may be contacted with a remover (removing agent or material) having an iodide-removability or iodide-adsorbability (e.g., a zeolite, an activated carbon, and an ion exchange resin). In order to efficiently remove the iodide from the acetic acid stream which is continuously obtained (in a continuous system), an ion exchange resin having iodide-removability or iodide-adsorbability, particularly an iodide-removing column provided with the ion exchange resin therein is advantageously used.

The ion exchange resin to be used is usually an ion exchange resin (usually a cation exchange resin) in which at least part of the active site (e.g., usually an acidic group such as a sulfone group, a carboxyl group, a phenolic hydroxyl group, or a phosphone group) is substituted or exchanged with a metal. The metal may include, for example, at least one member selected from the group consisting of silver (Ag), mercury (Hg), and copper (Cu). The cation exchange resin as a base (substrate) may be any one of a strong acidic cation exchange resin and a weak (mild) acidic cation exchange resin, and the preferred one includes a strong acidic cation exchange resin, for example, a macroreticular ion exchange resin, and the like.

In the ion exchange resin, the proportion of the active site exchanged to the metal (or substituted with the metal) may be, for example, about 10 to 80% by mol, preferably about 25 to 75% by mol, and more preferably about 30 to 70% by mol.

At least contacting of the acetic acid stream from the second distillation column with the ion exchange resin (preferably passing of the acetic acid stream through the ion exchange resin) achieves removal of the iodide. While contacting with (or passing through) the ion exchange resin, if necessary, the temperature of the acetic acid stream may be increased (or elevated) stepwise. The stepwise temperature elevation ensures to inhibit outflow or effusion of the metal from the ion exchange resin, as well as to remove the iodide efficiently.

Examples of the iodide-removing column may include a packed column packing inside thereof at least the ion exchange resin which is exchanged with a metal, a column provided with a bed of an ion exchange resin (e.g., a bed comprising a particulate resin) (a guard bed) and the like. The iodide-removing column may be provided with the metal-exchanged ion exchange resin, and in addition, another ion exchange resin (e.g., a cation exchange resin, an anion exchange resin, and a nonion exchange resin) inside thereof. Even when the metal is effused from the metal-exchanged ion exchange resin, arrangement of the cation exchange resin at the downstream side of the metal-exchanged ion exchange resin (e.g., arrangement of the cation exchange resin by packing, or arrangement of the cation exchange resin as a resin bed) allows the effused metal to be captured with the cation exchange resin and be removed from the carboxylic acid stream.

The temperature of the iodide-removing column may be, for example, about 18 to 100° C., preferably about 30 to 70° C., and more preferably about 40 to 60° C.

The rate of the acetic acid stream to be passed through is not limited to a specific one, and may be, for example, in an iodide-removing column utilizing a guard bed, e.g., about 3 to 15 BV/h (bed volume per hour), preferably about 5 to 12 BV/h, and more preferably about 6 to 10 BV/h.

In the iodide-removing step, the acetic acid stream may be at least contacted with the metal-exchanged ion exchange resin. For example, the iodide-removing column may comprise a column provided with the metal-exchanged ion exchange resin and a column provided with another ion exchange resin. For example, the iodide-removing column may comprise an anion exchange resin column, and a metal-exchanged ion exchange resin column on the downstream side of the anion exchange resin column, or may comprise a metal-exchanged ion exchange resin column, and a cation exchange resin column on the downstream side of the metal-exchanged ion exchange resin column. The details of the former example can be referred by WO02/062740, and others.

(Acetaldehyde Separation Step)

When the fraction containing acetaldehyde generated by the reaction is recycled and circulated to the reaction system or others, the amount of by-product (s) such as propionic acid, an unsaturated aldehyde, or an alkyl iodide increases. Thus, it is preferred to remove acetaldehyde in the solution to be recycled. In particular, removal of acetaldehyde is preferred, because it is unnecessary to separate and remove propionic acid, which makes acetic acid sub-standard, in the second distillation column. The method for separating acetaldehyde may comprise feeding a recycle solution (a solution to be recycled) to the acetaldehyde-separating column to separate a lower boiling point fraction containing acetaldehyde and a higher boiling point fraction containing methyl iodide, methyl acetate, water, and others, and then separating acetaldehyde from the top or upper part of the aldehyde-separating column, with the offgas component (e.g., carbon monoxide and hydrogen). Further, the offgas component may be previously removed off with a condenser or a cooling unit, prior to the separation of acetaldehyde. Furthermore, since the higher boiling point fraction obtained by removing acetaldehyde as the lower boiling point fraction contains methyl iodide, water, methyl acetate, acetic acid, and the like, the higher boiling point fraction may be recycled to the reaction system.

As the aldehyde-separating column, for example, there may be used a conventional distillation column, e.g., a plate column, a packed column, a flash evaporator, and others.

The temperature (the temperature of the column top) and the pressure (the pressure of the column top)) in the acetaldehyde-separating column may be selected depending on the species of the distillation column and others, and is not particularly limited to a specific one as far as at least acetaldehyde is separable as a lower boiling point fraction from the recycle solution [for example, the lower boiling point fraction(s) obtained in the first and/or second distillation column(s)] by utilizing difference between acetaldehyde and other components (particularly methyl iodide) in boiling point. For example, for the plate column, the pressure may be about 0.01 to 1 MPa, preferably about 0.01 to 0.7 MPa, and more preferably about 0.05 to 0.5 MPa as a gauge pressure. The inner temperature of the column is, for example, about 10 to 150° C., preferably about 20 to 130° C., and more preferably about 40 to 120° C. The theoretical number of plates may be, for example, about 5 to 150, preferably about 8 to 120, and more preferably about 10 to 100.

In the acetaldehyde-separating column, the reflux ratio may be selected from about 1 to 1000, preferably about 10 to 800, and preferably about 50 to 600 (e.g., about 70 to 400) depending on the above-mentioned theoretical number of plates.

EXAMPLES

The following examples are intended to describe this invention in further detail and should by no means be interpreted as defining the scope of the invention.

Comparative Example 1

In a continuous reaction process for acetic acid production, methanol was allowed to react with carbon monoxide in a carbonylation reactor, the reaction mixture obtained from the reactor was continuously fed to a flasher and subjected to flash distillation. The resulting volatile component at least containing product acetic acid, methyl acetate, methyl iodide, water, and hydrogen iodide was fed to a first distillation column, and a first lower boiling point component was separated as an overhead. To a second distillation column (number of plates: 50, charging plate: 30th plate from bottom), 100 parts of a first liquid stream having a composition of 3.0% by weight of methyl iodide (MeI), 2.0% by weight of methyl acetate (MA), 2.0% by weight of water ($H_2O$), 20 ppm (on the basis of weight) of hydrogen iodide (HI), and 93.0% by weight of acetic acid (the liquid temperature of the first liquid stream: 130° C.) was fed; and a lower boiling point impurity (second lower boiling point component) was distilled and removed at a gauge pressure of 150 kPA, a column bottom temperature of 160° C., a column top temperature of 145° C., and a reflux ratio of 2 in a proportion of 26 parts of a second lower boiling point component (distillate) and 74 parts of a second liquid stream containing acetic acid (bottom fraction). The second lower boiling point component (distillate) was circulated to the reaction system, and the crude acetic acid (second liquid stream) as the bottom fraction after purification was subjected to a further purification by the next distillation column. The composition (formulation) of the second lower boiling point component (distillate) was as follows: 11.4% by weight of MeI, 7.7% by weight of MA, 7.6% by weight of $H_2O$, 40 ppm of HI, and 75.1% by weight of acetic acid (Ac).

In the continuous reaction process, test pieces were added to the column top of the second distillation column. After leaving for 100 hours, each test piece was examined for a corrosion test, and the corrosion of each test piece was observed before and after the corrosion test.

The corrosion test was evaluated on the basis of the following criteria in Comparative Examples 1 and 3 and Examples 1 to 3 and evaluated on the observed corrosion amount in Comparative Example 2 and Examples 4 to 6.
"A": Test piece is not corroded at all.
"B": Test piece is hardly corroded.
"C": Test piece is slightly corroded.
"D": Test piece is significantly corroded.

Example 1

The process was performed in the same manner as in Comparative Example 1 except that potassium hydroxide (KOH) was so added to the first liquid stream to have a proportion of 0.07% by weight in the resulting mixture (liquid object) and that the mixture was fed (charged) to the second distillation column, and the corrosion test was performed. The liquid temperature of the first liquid stream did not change after the addition of potassium hydroxide. The time from when the potassium hydroxide was added to the first liquid stream till when the mixture was fed to the second distillation column was 30 seconds. The composition of the distillate did not change except that the concentration of HI was 5 ppm.

Example 2

The process was performed in the same manner as in Comparative Example 1 except that potassium hydroxide (KOH) was so added to the first liquid stream to have a proportion of 0.02% by weight in the resulting mixture (liquid object) and that the mixture was fed (charged) to the second distillation column, and the corrosion test was performed. The liquid temperature of the first liquid stream did not change after the addition of potassium hydroxide. The time from when the potassium hydroxide was added to the first liquid stream till when the mixture was fed to the second distillation column was 30 seconds. The composition of the distillate did not change except that the concentration of HI was 10 ppm.

Example 3

The process was performed in the same manner as in Comparative Example 1 except that potassium hydroxide (KOH) was so added to the first liquid stream to have a proportion of 0.04% by weight in the resulting mixture (liquid object) and that the mixture was fed (charged) to the second distillation column, and the corrosion test was performed. The liquid temperature of the first liquid stream did not change after the addition of potassium hydroxide. The time from when the potassium hydroxide was added to the first liquid stream till when the mixture was fed to the second distillation column was 30 seconds. The composition of the distillate did not change except that the concentration of HI was 20 ppm.

Comparative Example 2

The process was performed in the same manner as in Comparative Example 1 except that 100 parts of the first liquid stream having a composition of 3.0% by weight of MeI, 2.0% by weight of MA, 0.6% by weight of $H_2O$, 20 ppm of HI (on the base of weight), and 94.4% by weight of acetic acid was used, and the corrosion test was performed. The composition of the second lower boiling point component (distillate) was as follows: 11.0% by weight of MeI, 7.9% by weight of MA, 2.1% by weight of $H_2O$, and 42 ppm of HI; and the remainder was acetic acid.

Example 4

The process was performed in the same manner as in Comparative Example 2 except that potassium hydroxide (KOH) was so added to the first liquid stream to have a proportion of 0.07% by weight in the resulting mixture (liquid object) and that the mixture was fed (charged) to the second distillation column, and the corrosion test was performed. The liquid temperature of the first liquid stream did not change after the addition of potassium hydroxide. The time from when the potassium hydroxide was added to the first liquid stream till when the mixture was fed to the second distillation column was 30 seconds. The composition of the distillate was as follows: 11.5% by weight of MeI, 7.2% by weight of MA, 2% by weight of $H_2O$, and less than 5 ppm of HI; and the remainder was acetic acid.

Example 5

The process was performed in the same manner as in Comparative Example 2 except that potassium hydroxide (KOH) was so added to the first liquid stream to have a proportion of 0.02% by weight in the resulting mixture (liquid object) and that the mixture was fed (charged) to the second distillation column, and the corrosion test was performed. The liquid temperature of the first liquid stream did not change after the addition of potassium hydroxide. The time from when the potassium hydroxide was added to the first liquid stream till when the mixture was fed to the second distillation column was 30 seconds. The composition of the distillate was as follows: 11.7% by weight of MeI, 7.4% by weight of MA, 2.2% by weight of $H_2O$, and 11 ppm of HI; and the remainder was acetic acid.

Example 6

The process was performed in the same manner as in Comparative Example 2 except that potassium hydroxide (KOH) was so added to the first liquid stream to have a proportion of 0.04% by weight in the resulting mixture (liquid object) and that the mixture was fed (charged) to the second distillation column, and the corrosion test was performed. The liquid temperature of the first liquid stream did not change after the addition of potassium hydroxide. The time from when the potassium hydroxide was added to the first liquid stream till when the mixture was fed to the second distillation column was 30 seconds. The composition of the distillate was as follows: 11.1% by weight of MeI, 7.0% by weight of MA, 2.1% by weight of $H_2O$, and 19 ppm of HI; and the remainder was acetic acid.

The composition of the distillate and the results of the corrosion test are shown in Table. The details of the materials described in Table are as follows. The unit "mm/Y" means the corrosion rate of the test piece per year (the decreased thickness (mm) of the test piece per year).

HB2: HASTELLOY B2 (nickel-based alloy), manufactured by Oda Koki Co., Ltd.

HC: HASTELLOY C (nickel-based alloy), manufactured by Oda Koki Co., Ltd.

TABLE 1

| | Composition of distillate | | | | | Charge condition of KOH | | Corrosion test | |
|---|---|---|---|---|---|---|---|---|---|
| | MeI wt % | MA wt % | $H_2O$ wt % | HI ppm | AC wt % | KOH wt % | KOH/HI molar ratio | HB2 mm/Y | HC mm/Y |
| Comparative Example 1 | 11.4 | 7.7 | 7.6 | 40 | remainder | 0 | 0 | B | D |
| Example 1 | 11.4 | 7.7 | 7.6 | 5 | remainder | 0.07 | 76 | A | B |
| Example 2 | 11.4 | 7.7 | 7.6 | 10 | remainder | 0.02 | 22 | A | C |
| Example 3 | 11.4 | 7.7 | 7.6 | 20 | remainder | 0.04 | 22 | A | C |
| Comparative Example 2 | 11.0 | 7.9 | 2.1 | 42 | remainder | 0 | 0 | 0.09 | 0.15 |
| Example 4 | 11.5 | 7.2 | 2 | less than 5 | remainder | 0.07 | 76 | less than 0.03 | 0.05 |
| Example 5 | 11.7 | 7.4 | 2.2 | 11 | remainder | 0.02 | 23 | 0.04 | 0.08 |
| Example 6 | 11.1 | 7.0 | 2.1 | 19 | remainder | 0.04 | 21 | 0.05 | 0.1 |

INDUSTRIAL APPLICABILITY

The production process of the present invention is extremely useful as a process for producing acetic acid while efficiently inhibiting the increased concentration (or condensation) of hydrogen iodide in the second distillation column.

DESCRIPTION OF REFERENCE NUMERALS

1 . . . Reactor
2 . . . Flasher (evaporator)
3 . . . First distillation column
4 . . . Second distillation column
5, 6, 7, 8, 9 . . . Condenser or heat exchanger
10 . . . Scrubber system

The invention claimed is:

1. A process for producing acetic acid, which process comprises
an acetic acid collection step for feeding a first distillation column with a volatile component at least containing acetic acid, methyl acetate, methyl iodide, water, and hydrogen iodide, separating a first lower boiling point component as an overhead, collecting a first liquid stream containing acetic acid, and
an acetic acid purification step for feeding a second distillation column with the first liquid stream, further separating a second lower boiling point component as an overhead, and collecting a second liquid stream containing acetic acid, wherein in the second distillation column, a mixture is distilled, the mixture containing: the first liquid stream which further contains methyl iodide in a concentration of 10 ppm to 8% by weight and water in a concentration of 0.2 to 20% by weight; at least one component (A) having a boiling point lower than a boiling point of acetic acid and being selected from the group consisting of alcohol, ether, and acetate ester; and an alkali component,
wherein the component (A) is added to the first liquid stream in the following manners (i) and/or (ii) for presenting the component (A) in the mixture in a concentration of 0.1 to 15% by weight:
(i) the component (A) is added to the first liquid stream before the first liquid stream is fed to the second distillation column;
(ii) in the second distillation column, the component (A) is added to the first liquid stream at the same height level as a height level at which the first liquid stream is fed or at a height level greater than the height level at which the first liquid stream is fed, and
wherein the alkali component is added or mixed in the following manners (1) and/or (2):
(1) the alkali component is added to or mixed with the first liquid stream before the first liquid stream is fed to the second distillation column,
(2) in the second distillation column, the alkali component is added or mixed at the same height level as a height level at which the first liquid stream is fed or at a height level greater than the height level at which the first liquid stream is fed.

2. The process according to claim 1, wherein, in the first liquid stream, a concentration of methyl acetate is 0.1 to 8% by weight, a concentration of hydrogen iodide is not more than 1000 ppm on the basis of weight, an amount to be added of the alkali component is 1 to 2000 molar equivalents relative to 1 mol of hydrogen iodide in the first liquid stream, and the alkali component is added in order that the concentration of the alkali component in the mixture is not more than 100,000 ppm on the basis of weight.

3. The process according to claim 2, wherein, in the first liquid stream, the concentration of methyl iodide is less than 4% by weight.

4. The process according to claim 2, wherein, in the first liquid stream, the concentration of methyl iodide is 10 ppm to 3.5% by weight.

5. The process according to claim 2, wherein, in the first liquid stream, the concentration of water is not more than 3% by weight.

6. The process according to claim 2, wherein, in the first liquid stream, the concentration of hydrogen iodide is not more than 100 ppm on the basis of weight.

7. The process according to claim 2, wherein, in the first liquid stream, the concentration of hydrogen iodide is 1 to 30 ppm on the basis of weight.

8. The process according to claim 1, wherein, in the manner (1), the contact temperature of the first liquid stream and the alkali component is 100 to 170° C., and the time from when the first liquid stream and the alkali component are mixed till when the mixture is fed to the second distillation column is not more than 5 minutes.

9. The process according to claim 1, wherein the amount to be added of the alkali component is not more than 85 molar equivalents relative to 1 mol of hydrogen iodide in the first liquid stream, and the alkali component is added in order that the concentration of the alkali component in the mixture may be not more than 1000 ppm on the basis of weight.

10. The process according to claim 1, wherein the amount to be added of the alkali component is not more than 80 molar equivalents relative to 1 mol of hydrogen iodide in the first liquid stream, and the alkali component is added in order that the concentration of the alkali component in the mixture may be not more than 800 pm on the basis of weight.

11. The process according to claim 1, wherein the component (A) exists at a concentration of not less than 1% by weight in the mixture.

12. The process according to claim 1, wherein the component (A) is allowed to exist in the mixture by adding the component (A) to the first liquid stream.

13. The process according to claim 1, wherein the material of the second distillation column comprises a nickel-based alloy.

14. A process for producing acetic acid, which comprises:
(a) carbonylating methanol with carbon monoxide at a temperature of 150 to 250° C. and a pressure of 15 to 40 atmospheres in the presence of a catalyst system while feeding carbon monoxide into the reaction system at a hydrogen partial pressure of 0.5 to 200 kPa;
(b) separating the reaction mixture into a volatile component and a liquid catalyst mixture;
(c) feeding a first distillation column with the volatile component obtained from the step (b), said volatile component containing at least acetic acid, methyl acetate, methyl iodide, water, and hydrogen iodide;
(d) separating a first lower boiling point component as an overhead;
(e) collecting a first liquid stream containing acetic acid;
(f) feeding a second distillation column with said first liquid stream;
(g) further separating a second lower boiling point component as an overhead; and
(h) collecting a second liquid stream containing acetic acid,
wherein in the second distillation column, a mixture is distilled, the mixture containing: the first liquid stream which further contains methyl iodide in a concentration of 10 ppm to 8% by weight and water in a concentration of 0.2 to 20% by weight, at least one component (A) having a boiling point lower than a boiling point of acetic acid and being selected from the group consisting of alcohol, ether, and acetate ester, and an alkali component,
wherein the component (A) is added to the first liquid stream in the following manners (i) and/or (ii) for presenting the component (A) in the mixture in a concentration of 0.1 to 15% by weight:
(i) the component (A) is added to the first liquid stream before the first liquid stream is fed to the second distillation column;
(ii) in the second distillation column, the component (A) is added to the first liquid stream at the same height level as a height level at which the first liquid stream is fed or at a height level greater than the height level at which the first liquid stream is fed, and
wherein the alkali component is added or mixed in the following manners (1) and/or (2):
(1) adding the alkali component to or mixing the alkali component with the first liquid stream before the first liquid stream is fed to the second distillation column;
(2) in the second distillation column, adding the alkali component at or mixing the alkali component at a height level equal to or greater than a height level at which the first liquid stream is fed.

* * * * *